(12) United States Patent
Sheen

(10) Patent No.: US 7,084,323 B1
(45) Date of Patent: Aug. 1, 2006

(54) STRESS-PROTECTED TRANSGENIC PLANTS

(75) Inventor: Jen Sheen, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 08/989,881

(22) Filed: Dec. 12, 1997

Related U.S. Application Data

(60) Provisional application No. 60/032,966, filed on Dec. 13, 1996.

(51) Int. Cl.
*C12N 15/82* (2006.01)
*C12N 15/29* (2006.01)
*A01H 5/00* (2006.01)
*A01H 5/10* (2006.01)

(52) U.S. Cl. ..................... 800/289; 800/298; 536/23.6; 435/252.3; 435/320.1; 435/419; 435/468

(58) Field of Classification Search ............... 435/69.1, 435/468, 410, 419, 320.1, 430, 252.3; 536/23.1, 536/23.6; 800/278, 283, 290, 295, 298, 289
See application file for complete search history.

(56) References Cited

FOREIGN PATENT DOCUMENTS

WO    WO 95 05731    3/1995
WO    WO 96 38566    12/1996

OTHER PUBLICATIONS

Urao et al. Mol. Gen. Genet. 1994. vol. 331-340, 1994.*
Gordon-Kamm et al. The Plant Cell. 1990. vol. 2: 603-618, 1990.*
Saijo et al. cDNA cloning and prokaryotic expression of maize calcium-dependent protein kinases. Biochimica et Biophysica Acta, 1997, vol. 1350: 109-114.*
Saijo et al. Over-expression of a single calcium-dependent protein kinase confers both cold and salt/drought tolerance on rice plants. Plant Journal, 2000, vol. 23: 319-327.*
Urao et al. Two genes that encode calcium-dependent protein kinases are induced by drought and high-salt stresses in *Arabidopsis thaliana*. Mol. Gen. Genet. 1994, vol. 244, pp. 331-340.*
Liu et al. Two transcription factors, DREB-1 and DREB-2, with an EREBP?AP2 DNA binding domain seperate two cellular sign transduction pathways in drought and low temperature respinsive gene expression, . . . The Plant Cell, 1998, vol. 10, pp. 139 1406.*
Murata N. et al. Genetically engineered alteration in the chilling sensitivity of plants. Nature. Apr. 23, 1992, vol. 356, pp. 710-713.*
Estruch et al., "Cloning and Characterization of a Maize Pollen-Specific Calcium-Dependent Calmodulin-Indepen-
dent Protein Kinase," Proc. Natl. Acad. Sci. 91:8837-8841 (1994).
Lin et al., "Molecular Cloning of a Brain-Specific Calcium/Calmodulin-Dependent Protein Kinase," Proc. Natl. Acad. Sci. 84:5962-5966 (1987).
Valvekens et al., "Agrobacterium Tumefaciens-Mediated Transformation of *Arabidopsis thaliana* Root Explants byUsing Kanamycin Selection," Proc. Natl. Acad. Sci. 85:5536-5540 (1988).
Bohnert et al., "Adaptations to Environmental Stresses," The Plant Cell 7:1099-1111 (1995).
Bray, Elizabeth A., "Molecular Responses to Water Deficit," Plant Physiol. 103:1035-1040 (1993).
Daugherty et al., "*Arabidopsis thaliana* as a Model for Studying Mechanisms of Plant Cold Tolerance," J. Biol. Chem. 267:8707-8710 (1994).
Holstrom et al., "Drought Tolerance in Tobacco," Nature 379:683-684 (1996).
Ingram et al., "The Molecular Basis of Dehydration Tolerance in Plants," Annu. Rev. Plant Physiol. Plant Mol. Biol. 47:377-403 (1996).
Kapiloff et al., "Calcium Calmodulin-Dependent Protein Kinase Mediates a Pathway for Transcriptional Regulation," Proc. Natl. Acad. Sci. U.S.A. 88:3710-3714 (1991).
Lillius et al., "Enhanced NaCl Stress Tolerance in Transgenic Tobacco Expressing Bacterial Choline Dehydrogenase," Bio/Technology 14:177-180 (1996).
Lin et al., "Molecular Cloning of a Brain-Specific Calcium/Calmodulin-Dependent Protein Kinase," Proc. Natl. Acad. Sci. USA 84:5962-5966 (1987).
Murata et al., "Genetically Engineered Alteration in the Chilling Sensitivity of Plants," Nature 356:710-712 (1992).
Shen et al., "Modular Nature of Abscisic Acid (ABA) Response Complexes: Composite Promoter Units That Are Necessary and Sufficient for ABA Induction of Gene Expression in Barley," The Plant Cell 8:1107-1119 (1996).
Skriver et al., "Gene Expression in Response to Abscisic Acid and Osmotic Stress," The Plant Cell 2:503-512 (1990).
Tarczynski et al. "Expression of a Bacterial mtld Gene in Transgenic Tobacco Leads Production and Accumulation of Mannitol," Proc. Natl. Acad. Sci. USA 89:2600-2604 (1992).
Tarczynski et al., "Stress Protection of Transgenic Tobacco by Production of the Osmolyte Mannitol," Science 259:508-510 (1993).
Tomos, D., "Life Without Water," Current Biology 2:594-596 (1992).

(Continued)

*Primary Examiner*—Cynthia Collins
(74) *Attorney, Agent, or Firm*—Clark & Elbing LLP

(57) ABSTRACT

Disclosed are methods for increasing a plant's tolerance to environmental stress.

19 Claims, 14 Drawing Sheets

OTHER PUBLICATIONS

Urao et al., "Two genes That Encode $Ca^{2+}$ Dependent Protein Kinases Are Induced by Drought and High-Salt Stresses in *Arabidopsis thaliana*," Mol. Gen. Genet. 244:331-340 (1994).

Xu et al., "Expression of a Late Embryogenesis Abundant Protein Gene, HVA1, from Barley Confers Tolenrance to Water Deficit and Salt Stress in Transgenic Rice," Plant Physiol. 110:249-257 (1996).

Felix et al., "Rapid Changes of Protein Phosphorylation are Involved in Transduction of the Elicitor Signal in Plant Cells," *Proc. Nat. Acad. Sci. USA* 88:8831-8834 (1991).

Hughes et al., "Complementation of byr1 in Fission Yeast By Mammalian MAP Kinase Kinase Requires Coexpression of Raf Kinase," *Nature* 364:349-352 (1993).

Ito et al., "NPK15, a Tobacco Protein-Serine/Threonine Kinase with a Single Hydrophobic Region Near the Amino-Terminus," *Mol. Gen. Genet.* 245:1-10 (1994).

Nakashima et al., "The Expression Pattern of the Gene for NPK1 Protein Kinase Related to Mitogen-Activated Protein Kinase Kinase Kinase (MAPKKK) in a Tobacco Plant: Correlation with Cell Proliferation," *Plant Cell Physiology* 39:390-700 (1998).

Nishihama et al., "Possible Involvement of Differential Splicing in Regulation of the activity of *Arabidopsis* ANP1 that is Related to Mitogen-Activated Protein Kinase Kinase Kinase," *The Plant Journal* 12:39-48 (1997).

Saijo et al., "cDNA cloning and prokaryotic expression of maize calcium-dependent protein kinases," *Biochimica et Biophysica Acta* 1350:109-114 (1997).

Saijo et al., "Over-expression of a single $CA^{2+}$-dependent protein kinase confers both cold and salt/drought tolerance on rice plants," *The Plant Journal* 23:319-327 (2000).

Seo et al., "Tobacco MAP Kinase: A Possible Mediator in Wound Signal Transduction Pathways," *Science* 270:1988-1992 (1995).

Song et al., "A Receptor Kinase-Like Protein Encoded by the Rice Disease Resistance Gene, Xa21," *Science* 270:1804-1806 (1995).

Watillon et al., "A Calcium/Calmodulin-Binding Serine/Threonine Protein Kinase Homologous to the Mammalian Type II Calcium/Calmodulin-Dependent Protein Kinase Is Expressed in Plant Cells," *Plant Physiology* 101:1381-1384 (1993).

Bartels et al., "Approaches to improve stress tolerance using molecular genetics," *Plant, Cell and Environment* 17:659-667, 1994.

Botella et al., "Calcium-dependent protein kinase gene expression in response to physical and chemical stimuli in mungbean (*Vigna radiata*)" *Plant Molecular Biology* 30:1129-1137, 1996.

Hong et al., "Expression of three members of the calcium-dependent protein kinase gene family in *Arabidopsis thaliana*," *Plant Molecular Biology* 30:1259-1275, 1996.

Hrabak et al., "Characterization of eight new members of the calmodulin-like domain protein kinase gene family from *Arabidopsis thaliana*," *Plant Molecular Biology* 31:405-412, 1996.

* cited by examiner

FIG. 3B

PK Constructs

1. [35SC4PPDK] ATCDPK (AK1) 1 a.a. ATG ... 413 a.a. TGA | DHA | NOS
2. [35SC4PPDK] ATCDPK1 — 274 a.a. | DHA | NOS
3. [35SC4PPDK] ATCDPK1a — 274 a.a. | DHA | NOS
4. [35SC4PPDK] ATCDPK2 — 289 a.a. | DHA | NOS
5. [35SC4PPDK] ATPKa — 284 a.a. | DHA | NOS
6. [35SC4PPDK] ATPKb — 283 a.a. | DHA | NOS
7. [35SC4PPDK] ASK1 — 265 a.a. | DHA | NOS
8. [35SC4PPDK] ASK2 — 265 a.a. | DHA | NOS

FIG. 3C

FIG. 4A
FIG. 4B
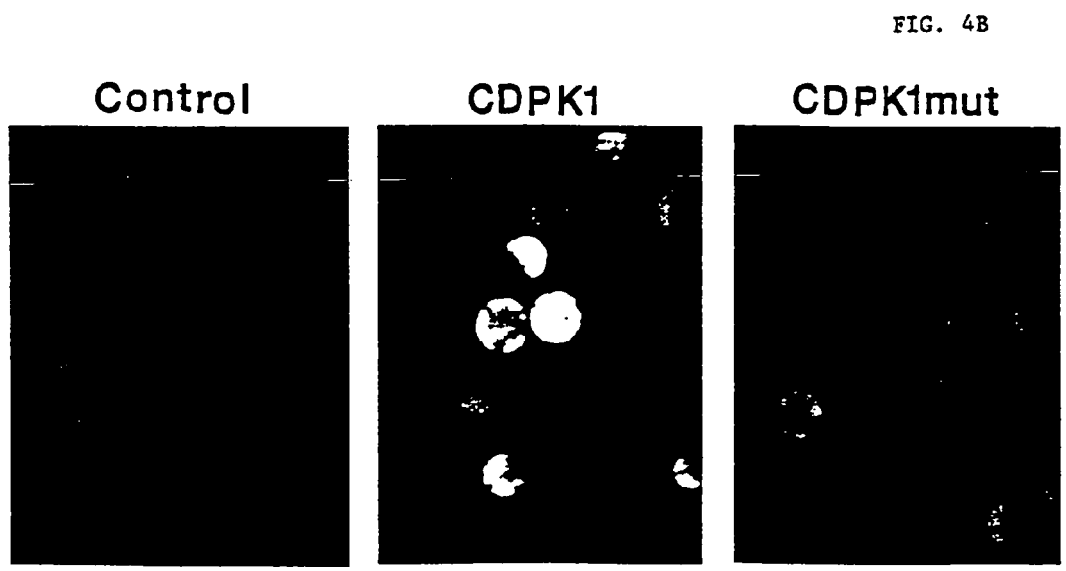

FIGURE 5 (SHEET 1/4)

```
SEQ ID NO:1   GTTGTAAAACGACGGNCAGTGAATTGTAATACGACTCNCTATAGGGCGNAATTGGAGCTC
         1   ------------+----------+----------+----------+----------+   60
              CAACATTTTGCTGCCNGTCACTTAACATTATGCTGAGNGATATCCCGCNTTAACCTCGAG
         a

CACCGCGGTGGCGGCCGCTCTAGAACTAGTGGATCCATGGCTAATCAAACTCAGATCAGC
         61  ------------+----------+----------+----------+----------+  120
              GTGGCGCCACCGCCGGCGAGATCTTGATCACCTAGGTACCGATTAGTTTGAGTCTAGTCG
                                                  SEQ ID NO:2   M  A  N  Q  T  Q  I  S  -

GACAAGTACATCTTAGGACGAGAACTCGGTCGCGGCGAATTCGGAATCACGTATCTTTGT
         121 ------------+----------+----------+----------+----------+  180
              CTGTTCATGTAGAATCCTGCTCTTGAGCCAGCGCCGCTTAAGCCTTAGTGCATAGAAACA
         a    -  D  K  Y  I  L  G  R  E  L  G  R  G  E  F  G  I  T  Y  L  C  -
```

FIGURE 5 (SHEET 2/4)

```
       ACAGATAGAGAGACTCGTGAAGCTTTAGCTTGCAAATCAATCTCCAAGAGAAAGCTCCGA
181    ------------------------------------------------------------ 240
       TGTCTATCTCTCTGAGCACTTCGAAATCGAACGTTTAGTTAGAGGTTCTCTTTCGAGGCT

T  D  R  E  T  R  E  A  L  A  C  K  S  I  S  K  R  K  L  R    -

ACCGCCGTCGATGTGGAAGACGTCCGTCGTGAAGTCACGATCATGTCAACTTTACCGGAA
241    ------------------------------------------------------------ 300
       TGGCGGCAGCTACACCTTCTGCAGGCAGCACTTCAGTGCTAGTACAGTTGAAATGGCCTT

T  A  V  D  V  E  D  V  R  R  E  V  T  I  M  S  T  L  P  E    -

CACCCAAACGTTGTGAAACTTAAAGCGACTTATGAGGATAACGAGACCGTGCATCTTGTG
301    ------------------------------------------------------------ 360
       GTGGGTTTGCAACACTTTGAATTTCGCTGAATACTCCTATTGCTCTGGCACGTAGAACAC

H  P  N  V  V  K  L  K  A  T  Y  E  D  N  E  T  V  H  L  V    -

ATGGAGCTTTGTGAAGGAGGTGAGCTTTTTGGTCGGATTGTTGCAAGAGGACATTATACA
361    ------------------------------------------------------------ 420
       TACCTCGAAACACTTCCTCCACTCGAAAAACCAGCCTAACAACGTTCTCCTGTAATATGT

M  E  L  C  E  G  G  E  L  F  G  R  I  V  A  R  G  H  Y  T    -

GAGCGTGCGGCGGCTACCGTCGCGAGAACGATCGCGGAAGTTGTGAGGATGTGTCATGTC
421    ------------------------------------------------------------ 480
       CTCGCACGCCGCCGATGGCAGCGCTCTTGCTAGCGCCTTCAACACTCCTACACAGTACAG

E  R  A  A  A  T  V  A  R  T  I  A  E  V  V  R  M  C  H  V    -
```

FIGURE 5 (SHEET 3/4)

```
         AATGGTGTTATGCATAGAGATTTGAAGCCTGAGAATTTCTTGTTTGCTAACAAGAAGGAG
   481   ------------+----------+----------+----------+----------+----------+  540
         TTACCACAATACGTATCTCTAAACTTCGGACTCTTAAAGAACAAACGATTGTTCTTCCTC a   , N  G  V  M  H  R  D  L  K  P  E  N  F  L  F  A  N  K  K  E   -
```

```
         AATTCTGCACTTAAGGCTATTGATTTTGGTTTATCTGTTCTCTTTAAACCTGGAGAGAGG
   541   ------------+----------+----------+----------+----------+----------+  600
         TTAAGACGTGAATTCCGATAACTAAAACCAAATAGACAAGAGAAATTTGGACCTCTCTCC a     N  S  A  L  K  A  I  D  F  G  L  S  V  L  F  K  P  G  E  R   -
```

```
         TTTACAGAGATTGTTGGAAGTCCTTATTATATGGCTCCAGAAGTGTTGAAGAGAAATTAT
   601   ------------+----------+----------+----------+----------+----------+  660
         AAATGTCTCTAACAACCTTCAGGAATAATATACCGAGGTCTTCACAACTTCTCTTTAATA a     F  T  E  I  V  G  S  P  Y  Y  M  A  P  E  V  L  K  R  N  Y   -
```

```
         GGACCAGAGGTTGATGTGTGGAGTGCTGGAGTTATCCTCTACATCTTGCTTTGTGGTGTT
   661   ------------+----------+----------+----------+----------+----------+  720
         CCTGGTCTCCAACTACACACCTCACGACCTCAATAGGAGATGTAGAACGAAACACCACAA a     G  P  E  V  D  V  W  S  A  G  V  I  L  Y  I  L  L  C  G  V   -
```

FIGURE 5 (SHEET 4/4)

```
       CCTCCGTTTTGGGCAGAGACTGAACAAGGTGTGGCTCTTGCCATCTTGAGGGGAGTTCTT
721    ------------------------------------------------------------  780
       GGAGGCAAAACCCGTCTCTGACTTGTTCCACACCGAGAACGGTAGAACTCCCCTCAAGAA

P  P  F  W  A  E  T  E  Q  G  V  A  L  A  I  L  R  G  V  L   -

GATTTTAAGAGAGATCCTTGGTCGCAGATATCAGAGAGCGCAAAGAGCCTTGTGAAGCAG
781    ------------------------------------------------------------  840
       CTAAAATTCTCTCTAGGAACCAGCGTCTATAGTCTCTCGCGTTTCTCGGAACACTTCGTC

D  F  K  R  D  P  W  S  Q  I  S  E  S  A  K  S  L  V  K  Q   -

ATGTTGGAACCTGATTCAACTAAGCGTTTGACTGCTCAGCAAGTTCTTGATCACCCTTGG
841    ------------------------------------------------------------  900
       TACAACCTTGGACTAAGTTGATTCGCAAACTGACGAGTCGTTCAAGAACTAGTGGGAACC

M  L  E  P  D  S  T  K  R  L  T  A  Q  Q  V  L  D  H  P  W   -

ATACAGAATGCAAAGAAAAGGATCAAGCTTATCGATACCGTCGACCTCGAGGGGGGGCCC
901    ------------------------------------------------------------  960
       TATGTCTTACGTTTCTTTTCCTAGTTCGAATAGCTATGGCAGCTGGAGCTCCCCCCCGGG

I  Q  N  A  K  K

GGTACCAGCTTTNGTTCCCTTTAGTGAGGGTTAATTTCGAGCTTGGCGTAATCATGTCAT
961    ------------------------------------------------------------  1020
       CCATGGTCGAAANCAAGGGAAATCACTCCCAATTAAAGCTCGAACCGCATTAGTACAGTA
```

STRESS-PROTECTED TRANSGENIC PLANTS

CROSS REFERENCE TO RELATED APPLICATIONS

This application claims benefit from provisional application 60/032,966, filed on Dec. 13, 1996.

STATEMENT AS TO FEDERALLY SPONSORED RESEARCH

This invention was made in part with Government funding, and the Government therefore has certain rights in the invention.

BACKGROUND OF THE INVENTION

This invention relates to the fields of plant genetic engineering and crop protection.

In both monocot and dicot plants, the stress hormone abscisic acid (ABA) or environmental stress conditions such as drought, cold, and salinity can induce the expression of a number of highly conserved genes in vegetative tissues. The accumulation of these gene products is thought to protect plants from stress induced damage. Many of these genes are also expressed at the late stage of embryogenesis during seed development and are thought to be important for seed desiccation and dormancy. Several studies have identified cis-acting elements and trans-acting factors important for the regulation of these stress-inducible genes. Background information relating to the aforementioned topics is found in the following references: Skriver and Mundy, Plant Cell 2:503, 1990; Bray, Plant Physiol. 103:1035, 1993; Thomas and Bohnert, Plant Physiol. 103:1299, 1993; Chandler and Robertson, Ann. Rev. Plant Physiol. Plant Mol. Biol. 45:113, 1994; Daugherty et al., In *Arabidopsis*, Somerville and Meyerowitz, Eds. (CSH, CSHL, 1994), pp. 769–806; Finkelstein and Zeevaart, In *Arabidopsis*, Somerville and Meyerowtiz Eds. (CSH, CSHL 1994), pp. 523–553; Giraudat et al., Plant Mol. Biol. 26, 1957, 1994; Rock and Quantrano, Curr. Biol. 4:1013, 1994; Thomashow, In *Arabidopsis*, Somerville and Meyerowitz, Eds. (CSH, CSHL, 1994) pp. 807–834; Gosti et al., Mol. Gen. Genet. 246:10, 1995; and Knight et al., Plant Cell 7:499, 1995; Xu et al., Plant Physiol. 110:249, 1996; Guiltinan et al., Science 250:267, 1990; Finkelstein, Mol. Gen. Genet. 238:401, 1993; Thomas, Plant Cell 5:1401, 1993; Parcy et al., Plant Cell 6:1567, 1994; Hattori et al., Plant J. 7:913, 1995; Hoecker et al., Genes Dev. 9:2459, 1995; McCarty, Rev. Plant Physiol. Plant Mol. Biol. 46:71, 1995; Nambara et al., Development 121:629, 1995; Nakagawa et al., Plant J. 9:217, 1996; Hattori et al., Genes Dev. 6:609, 1992; Pla et al., Plant Mol. Biol. 24:701, 1994; Baker et al., Plant Mol. Biol. 24:701, 1994; Yamaguchi-Shinozaki and Shinozaki, Plant Cell 6:251, 1994; Menkens et al., Trend Biochem. Sci. 20:506, 1995; Shen and Ho, Plant Cell 7:295, 1995; Taylor et al., Plant J. 7:129, 1995; de Vetten and Ferl, Plant J. 7:589, 1995; and Lu et al., Plant Cell 8:847, 1996).

SUMMARY OF THE INVENTION

In general, the invention features a method for protecting a plant against an environmental stress, the method including the steps of: (a) producing a transgenic plant cell including a recombinant protein kinase (PK) domain gene integrated into the genome of the transgenic plant cell and positioned for expression in the plant cell; and (b) growing a transgenic plant from the plant cell, wherein the PK domain gene is expressed in the transgenic plant. In a preferred embodiment, the method of the invention involves the expression of a PK domain gene which is capable of increasing the level of tolerance to an environmental stress, e.g., dehydration, salt, or temperature stress. In other preferred embodiments, the invention includes a PK domain gene which encodes a polypeptide that includes an amino acid sequence that is substantially identical to the amino acid sequence of ATCDPK1 or ATCDPK1a. In still other preferred embodiments, the invention includes a gene encoding a polypeptide having a PK domain that includes an amino acid sequence that is substantially identical to the amino acid sequence of ATCDPK1 or ATCDPK1a.

In another aspect, the invention features a method for protecting a plant against environmental stress, the method including the steps of: (a) producing a transgenic plant cell including a recombinant calcium-dependent protein kinase (CDPK) gene integrated into the genome of the transgenic plant cell and positioned for expression in the plant cell, the CDPK gene being capable of increasing the level of tolerance to an environmental stress, e.g., dehydration, salt, and temperature stresses; and (b) growing a transgenic plant from the plant cell, wherein the CDPK gene is expressed in the transgenic plant.

In another aspect, the invention features a method for protecting a plant against environmental stress, the method including the steps of: (a) producing a transgenic plant cell including a recombinant calcium/calmodulin-dependent (CaM-K) gene integrated into the genome of the transgenic plant cell and positioned for expression in the plant cell; and (b) growing a transgenic plant from the plant cell wherein the CaM-K gene is expressed in the transgenic plant. In a preferred embodiment, the method of the invention includes the expression of a CaM-K gene (e.g., a mammalian CaM-KII gene) which is capable of increasing the level of tolerance to an environmental stress, e.g., against dehydration, salt, or temperature stress.

In yet another aspect, the invention features a method for protecting a plant against environmental stress, the method including the steps of: (a) producing a transgenic plant cell which includes a combination of at least two genes selected from the group consisting of a recombinant PK domain gene, a recombinant CDPK gene, and a CaM-K gene, each of the genes being integrated into the genome of the transgenic plant cell and positioned for expression in the plant cell; and (b) growing a transgenic plant from the plant cell, wherein each of the genes is expressed in the transgenic plant. In one preferred embodiment, the method of the invention includes the expression of genes which are capable of increasing the level of tolerance to an environmental stress, e.g., dehydration, salt, or temperature stress.

In another aspect, the invention features a transgenic plant including a recombinant PK domain gene integrated into the genome of the transgenic plant and positioned for expression in the plant, the PK domain gene being capable of increasing the level of tolerance to an environmental stress, e.g., dehydration, salt, or temperature stress, on a transgenic plant expressing the recombinant PK domain.

In another aspect, the invention features a transgenic plant including a recombinant CDPK gene integrated into the genome of the transgenic plant and positioned for expression in the plant, the recombinant CDPK gene being capable of increasing the level of tolerance to an environmental stress, e.g., dehydration, salt, or temperature stress, on a transgenic plant expressing the recombinant CDPK.

In another aspect, the invention features a transgenic plant including a recombinant CaM-K gene integrated into the genome of the transgenic plant and positioned for expression in the plant, the recombinant CaM-K gene being capable of increasing the level of tolerance to an environmental stress, e.g., dehydration, salt, or temperature stress, on a transgenic plant which is expressing the recombinant CaM-K gene.

In another aspect, the invention features a transgenic plant including a recombinant CDPK gene, PK domain gene, CaM-K gene, or any combination thereof integrated into the genome of the transgenic plant cell and positioned for expression in the plant cell, the CDPK, PK domain, and CaM-K genes being capable of increasing the level of tolerance to an environmental stress, e.g., dehydration, salt, or temperature stress, on a transgenic plant expressing the DNA.

In yet other aspects, the invention includes seeds and cells from any of the aforementioned transgenic plants.

In still other aspects, the invention features a substantially pure PK domain polypeptide capable of increasing the level of tolerance to an environmental stress, e.g., environmental stress in a transgenic plant. In one embodiment, the invention features a PK domain polypeptide including an amino acid sequence substantially identical to the amino acid sequence shown in FIG. 5 (SEQ ID NO: 2).

In another aspect, the invention features substantially pure DNA encoding a PK domain polypeptide capable of conferring tolerance to an environmental stress in a transgenic plant. This DNA may include a nucleic acid sequence substantially identical to the nucleic acid sequence shown in FIG. 5 (SEQ ID NO: 1). Such DNA may be operably linked to an expression control region for the expression of the PK polypeptide; and the expression control region may include a promoter (for example, a constitutive or inducible promoter).

In yet another aspect, the invention features a cell (e.g., a plant cell) which includes the DNA of the invention.

By "polypeptide" is meant any chain of amino acids, regardless of length or post-translational modification (for example, glycosylation or phosphorylation).

By "substantially identical" is meant a polypeptide or nucleic acid exhibiting at least 70%, preferably 80%, more preferably 85%, and most preferably 90%, or even 95% sequence identity to a reference sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, FastA, or PILEUP/PRETTYBOX programs). Such software matches identical or similar sequences by assigning degrees of homology to various substitutions, deletions, and/or other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

By a "substantially pure polypeptide" is meant a polypeptide (for example, the PK domain polypeptide shown in FIG. 5 (SEQ ID NO: 2)) that has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, a substantially pure polypeptide. For example, a substantially pure PK domain polypeptide may be obtained, for example, by extraction from a natural source (for example, a plant cell); by expression of a recombinant nucleic acid encoding a PK domain polypeptide; or by chemically synthesizing the protein. Purity can be measured by any appropriate method, for example, column chromatography, polyacrylamide gel electrophoresis, or by HPLC analysis.

By "derived from" is meant isolated from or having the sequence of a naturally-occurring sequence (e.g., a cDNA, genomic DNA, synthetic DNA, or combination thereof).

By "substantially pure DNA" is meant DNA that is free of the genes which, in the naturally-occurring genome of the organism from which the DNA of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) a regulator polypeptide (e.g., a CDPK, a PK domain, or a CaM-K polypeptide).

By "positioned for expression" is meant that the DNA molecule is positioned adjacent to a DNA sequence which directs transcription and translation, if appropriate, of the sequence (i.e., facilitates the production of, for example, a CDPK polypeptide, a PK domain polypeptide, a CaM-K polypeptide, a recombinant protein, or an RNA molecule).

By "reporter gene" is meant a gene whose expression may be assayed; such genes include, without limitation, β-glucuronidase (GUS), luciferase, chloramphenicol transacetylase (CAT), green fluorescent protein (GFP), and β-galactosidase.

By "expression control region" is meant any minimal sequence sufficient to direct transcription. Included in the invention are promoter elements that are sufficient to render promoter-dependent gene expression controllable for cell-, tissue-, or organ-specific gene expression, or elements that are inducible by external signals or agents (for example, light-, pathogen-, wound-, stress-, or hormone-inducible elements or chemical inducers such as SA or INA); such elements may be located in the 5' or 3' regions of the native gene or engineered into a transgene construct.

By "operably linked" is meant that a gene and a regulatory sequence(s) are connected in such a way as to permit gene expression when the appropriate molecules (for example, transcriptional activator proteins) are bound to the regulatory sequence(s).

By "plant cell" is meant any self-propagating cell bounded by a semi-permeable membrane and containing a plastid. Such a cell also requires a cell wall if further propagation is desired. Plant cell, as used herein includes, without limitation, algae, cyanobacteria, seeds, suspension cultures, embryos, meristematic regions, callus tissue, leaves, roots, shoots, gametophytes, sporophytes, pollen, and microspores.

By "crucifer" is meant any plant that is classified within the Cruciferae family. The Cruciferae include many agricultural crops, including, without limitation, rape (for example, *Brassica campestris* and *Brassica napus*), broccoli, cabbage, Brussel sprouts, radish, kale, Chinese kale, kohlrabi, cauliflower, turnip, rutabaga, mustard, horseradish, and *Arabidopsis*.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic plants and the DNA (transgene) is inserted by artifice into the nuclear or plastidic genome.

By "increased level of tolerance to environmental stress" is meant a greater level of tolerance to an environmental stress (e.g., drought, salinity, and temperature stress) than that exhibited by a control plant (for example, a non-transgenic plant). Preferably, the level of stress tolerance in a transgenic plant of the invention is at least 5%, 10%, or 20% (and preferably 30% or 40%) greater than the tolerance to an environmental stress exhibited in a control plant. In other preferred embodiments, the level of tolerance to an environmental stress is 50% greater, 60% greater, and more preferably even 75% or 90% greater than a control plant; with up to 100% above the level of tolerance as compared to a control plant being most preferred. The level of tolerance is measured using conventional methods. For example, the level of stress tolerance to salinity may be determined by comparing physical features and characteristics (for example, plant height and weight) of transgenic plants and control plants.

The invention provides a number of important advances and advantages for the protection of plants against environmental stress, such as drought, salt, and temperature. For example, the invention facilitates an effective and economical means to improve agronomically important traits of plants for tolerating the effects of dehydration, salinity, cold, and heat. The invention provides for increased production efficiency, as well as for improvements in quality and yield of crop plants and ornamentals. Thus, the invention contributes to the production of high quality and high yield agricultural products: for example, fruits, ornamentals, vegetables, cereals, and field crops. Genetically-improved seeds and other plant products that are produced using plants expressing the genes described herein also render farming possible in areas previously unsuitable for agricultural production. The invention further provides a means for mediating the expression of stress-related protective proteins that enable a plant to tolerate the effects of environmental stress. For example, transgenic plants constitutively producing a recombinant CDPK gene product, a PK domain, or CaM-K are capable of turning on a plant's stress signal transduction pathway by allowing the expression of multiple stress-related proteins, which in turn enhances the plant's tolerance to multiple stress conditions. Expression of these gene products therefore obviates the need to express individual stress-related genes as a means to promote plant defense mechanisms against adverse conditions.

Other features and advantages of the invention will be apparent from the following description of the preferred embodiments thereof, and from the claims.

DETAILED DESCRIPTION

The drawings will first be described.

Drawings

Figure 3A:
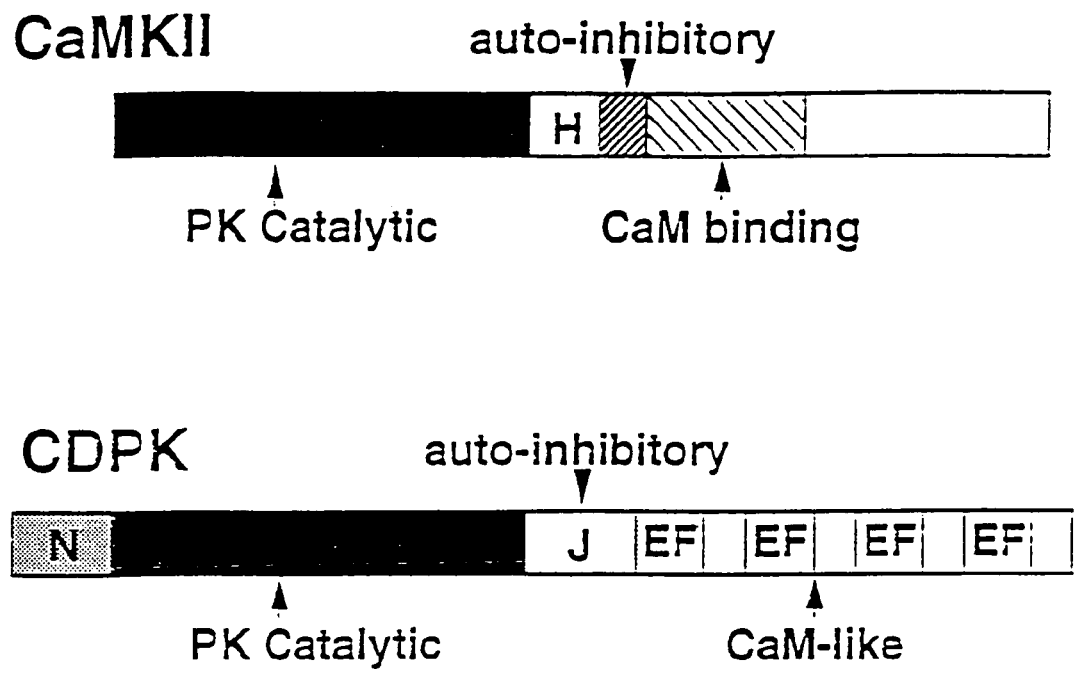
FIG. 3A shows a schematic illustration of the structural comparison between plant CDPKs and mammalian CaMKII.
Figure 3B:
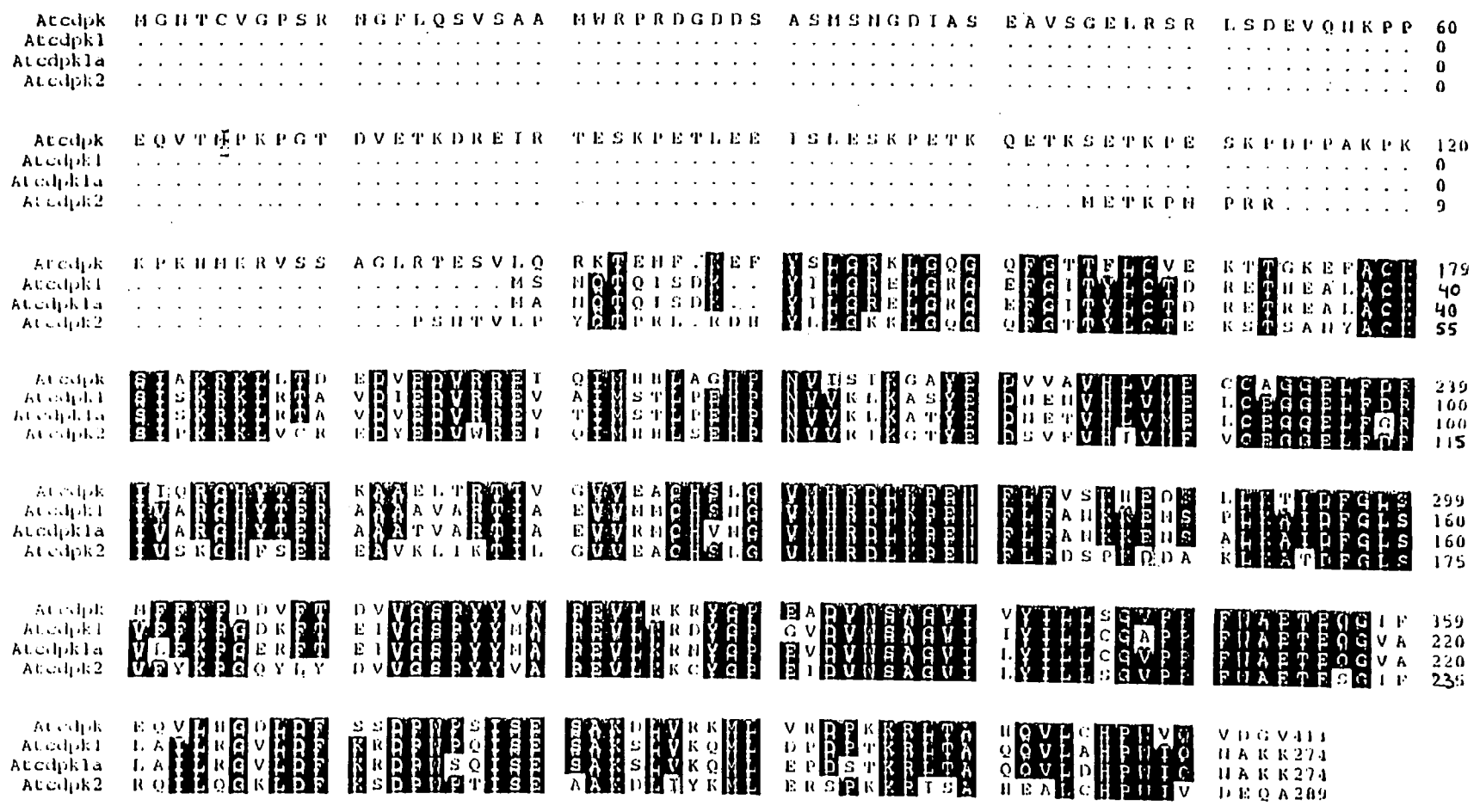
Figure 3D:
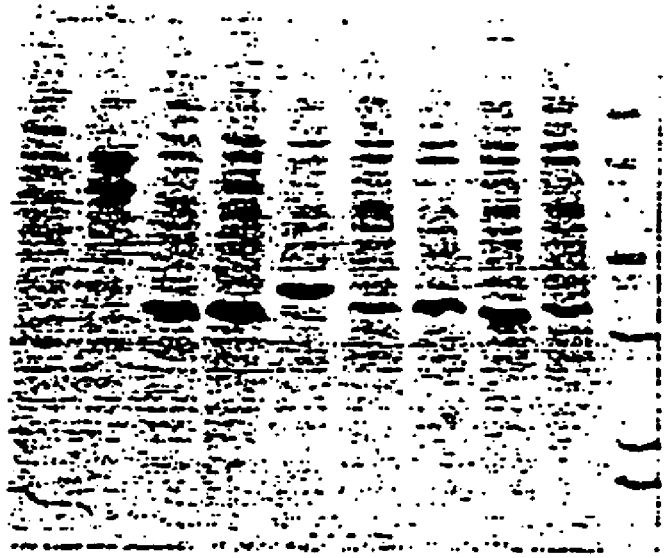
FIG. 3B shows the sequence comparison among the kinase domains of four ATCDPKs. Identical amino acids are highlighted.
FIG. 3C shows the schematic illustrations of various PK constructs.

FIG. 3D shows a photograph of a gel illustrating the immunoprecipitation of eight PKs with anti-HA. Lane 0, background control; Lane 1, ATCDPK; Lane 2, ATCDPK1; Lane 3, ATCDPK1a; Lane 4, ATCDPK2; Lane 5, ATPKa; Lane 6, ATPKb, Lane 7, ASK1; Lane 8, ASK2, Lane M, protein molecular weight markers (92, 66, 43, 27, 18, 14 kD).

Figure 3E:
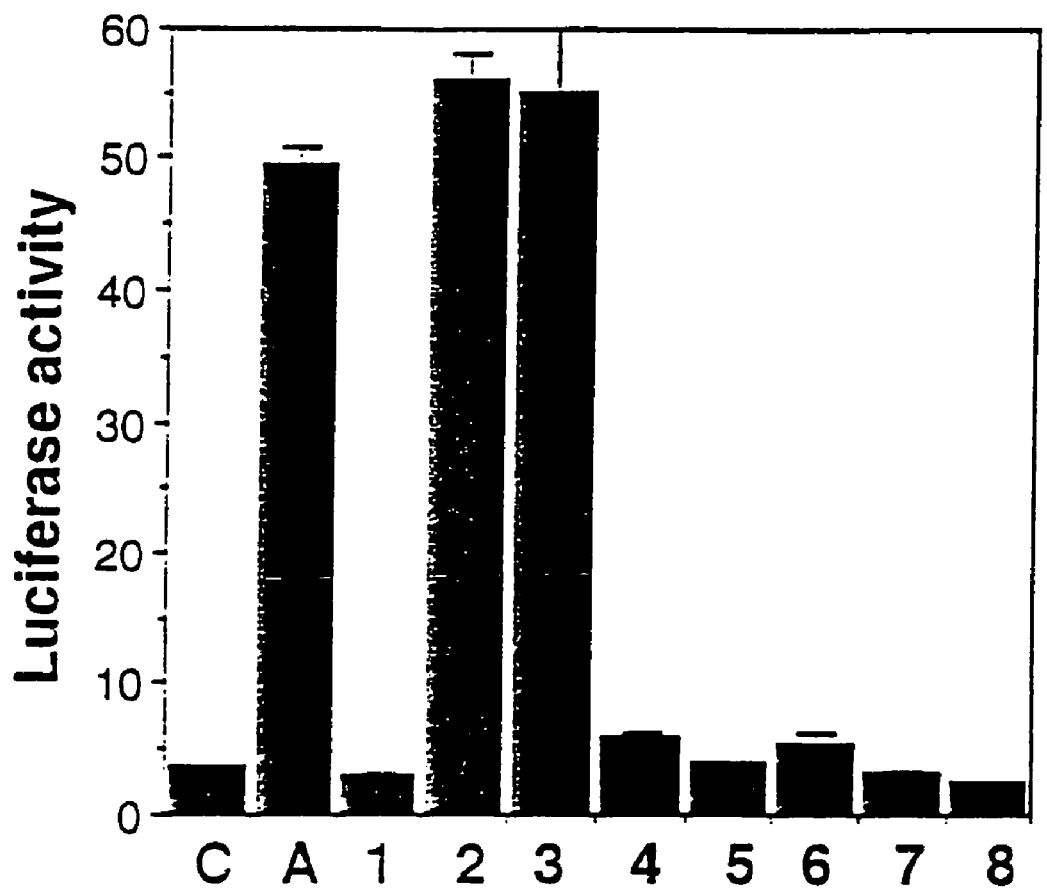

FIG. 3E shows a graph demonstrating that ATCDPK1 and ATCDPK1a activate stress-inducible transcription.

FIG. 4A shows a photograph of a gel illustrating the immunoprecipitation of ATCDPK1 and ATCDPK1(K40M) mutant proteins.

FIG. 4B shows a series of photographs demonstrating that the ATCDPK1 (K40M) mutant does not activate stress signaling.

Figure 4C:
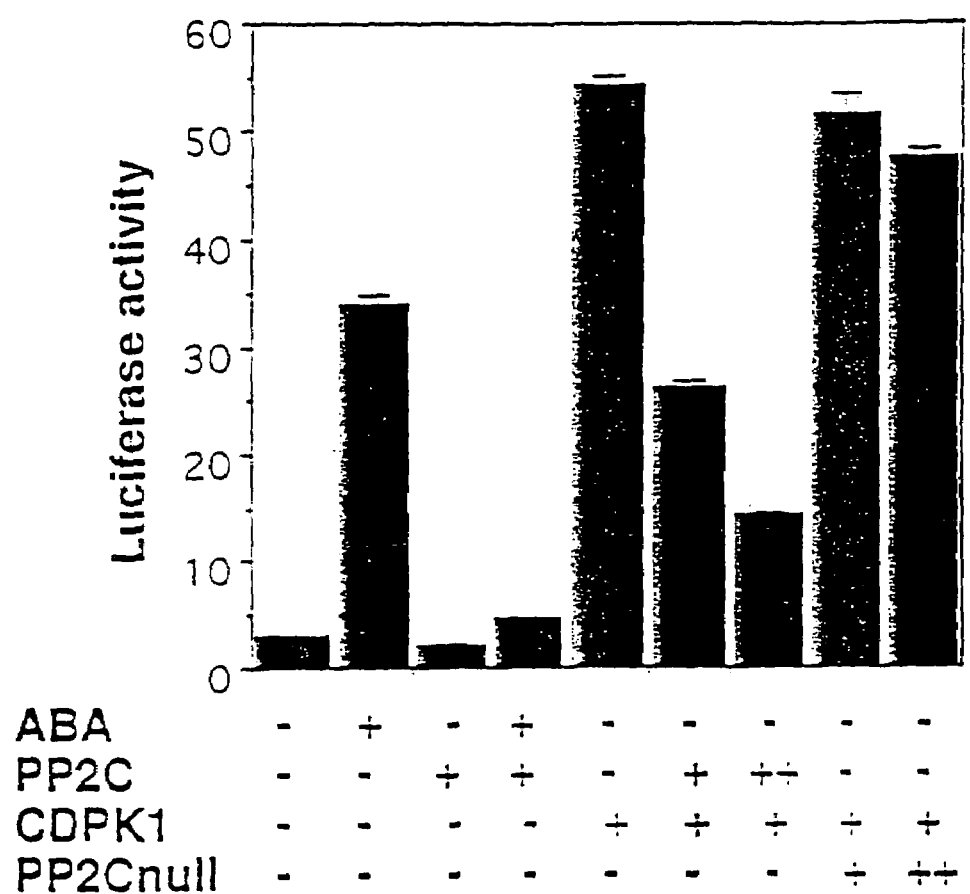

FIG. 4C shows a graph demonstrating that PP2C blocks the action of CDPK1.

Figure 4D:
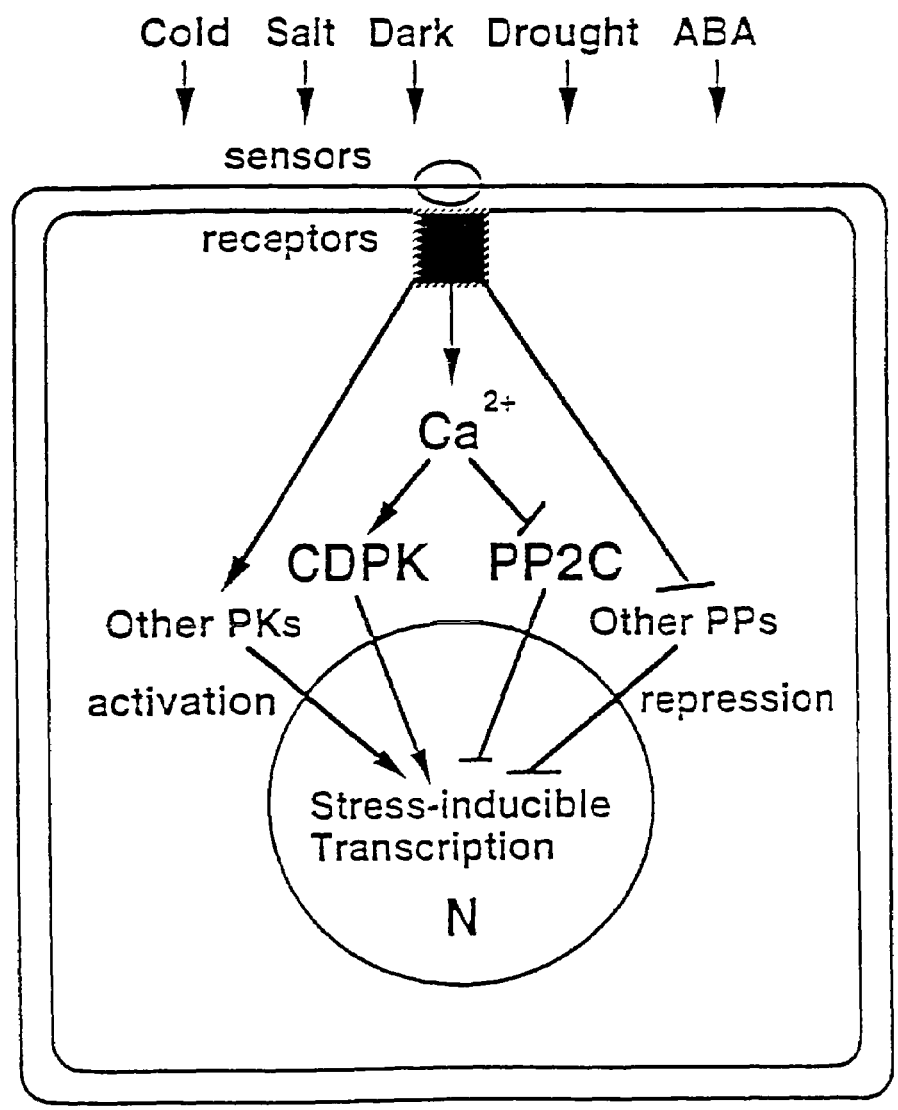

FIG. 4D shows a schematic illustration of a model for stress signal transduction in plant cells.

FIG. 5 shows the nucleotide and amino acid sequences of the ATCDPK1a PK domain, SEQ ID NO: 1 and SEQ ID NO: 2, respectively.

OVERVIEW

Evidence is presented below showing that constitutively active mutants of two closely related $Ca^{2+}$ dependent protein kinases (CDPK1 and CDPK1a) activate a stress-inducible promoter, bypassing stress signals. The effects of CDPK1 and CDPK1a are specific since six distinct plant protein kinases, including two other CDPKs, failed to mimic stress signaling. The activation is abolished by a CDPK1 mutation in the kinase domain, and diminished by a constitutively active protein phosphatase 2C capable of blocking the stress hormone ABA responses. The results indicate that CDPKs (including their PK domains) play distinct physiological roles. CDPK1 and CDPK1a are therefore examples of positive regulators for controlling stress signal transduction in plants. Expression of such regulators in transgenic plants is useful for turning on the stress signal transduction pathway as a means for increasing plant tolerance to multiple stress conditions, including drought, salinity, and extreme temperature conditions.

Stress Signaling in Maize Leaf Protoplasts Visualized by GFP Expression

Responses to multiple stress treatments were monitored using green-fluorescent protein (GFP) as a vital reporter (Chiu et al. Curr. Biol. 6:225, 1996), using a single cell maize leaf protoplast system (Sheen, EMBO J 12:3497, 1993). A chimeric gene was generated by fusing the stress-inducible CDPK HVA1 promoter (Straub et al., Plant Mol. Biol. 26:617, 1994) to a synthetic GFP sequence (HVA1-SGFP) (Chiu et al. Curr. Biol. 6:225, 1996). The barley HVA1 promoter was obtained by PCR using barley genomic DNA and two primers: 5'TCCACCGAGATGCCGACGCA-3' (SEQ ID NO: 17) and 5'-GTTGGAGGCCATG-GTCGTCTCACGAT-3' (SEQ ID NO: 18). The HVA1 promoter and the SGFP were fused at the ATG NcoI site. The CDPK HVA1 gene has been reported to be activated by multiple stress signals in vegetative tissues (Straub et al., Plant Mol. Biol. 26:617, 1994). Four clones were selected and tested for stress responses with identical results as is discussed below.

Figure 1:
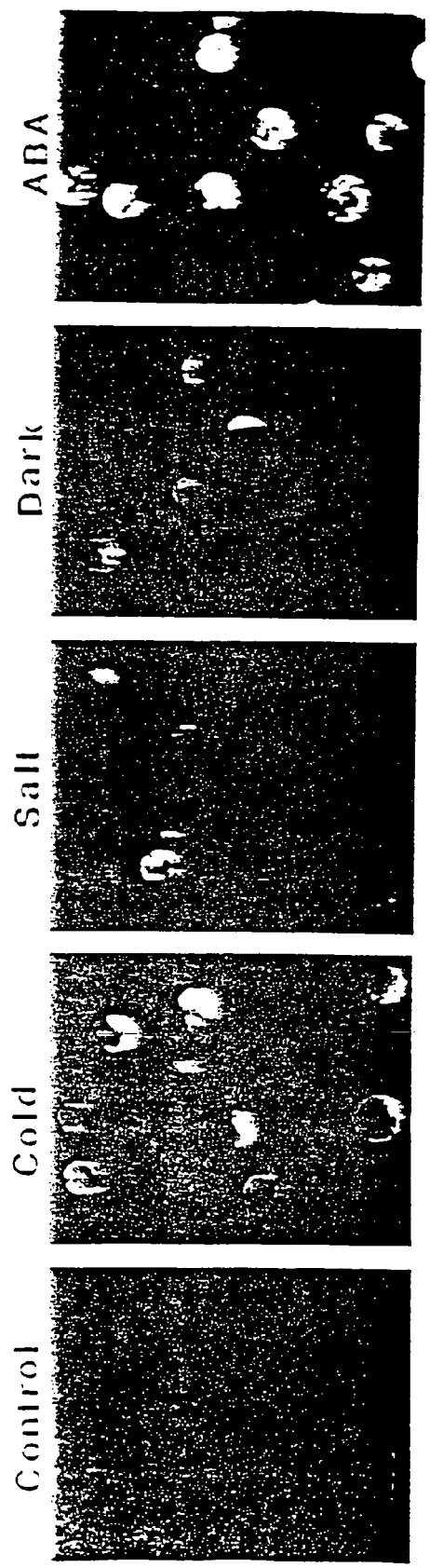
FIG. 1 shows a series of photographs demonstrating stress signaling in maize leaf protoplasts as visualized by green-fluorescent (GFP) expression.

Maize leaf protoplasts were electroporated with the plasmid DNA carrying HVA1-SGFP and divided ($10^5$ cells/ml per sample) for various treatments: constant light (15 $\mu Em^{-2}S^{-1}$) at 23° C. for sixteen hours (Control), 0° C. for four hours followed by twelve hours at 23° C. (Cold), 0.2 M NaCl for three hours, washed, and incubated for thirteen hours (Salt), constant darkness for sixteen hours (Dark), and 100 μM ABA for sixteen hours (ABA) (FIG. 1). The protocol for transient expression analysis using maize leaf protoplasts has been described by Sheen (EMBO J. 12:3497, 1993) and Chiu et al. (Curr. Biol. 6:225, 1996). About $10^5$ protoplasts from each treatment were observed using a fluorescence microscope as described by Chiu et al. (Curr. Biol. 6:225, 1996). The experiment was repeated three times with similar results. About 50% of the protoplasts, showing green/yellow fluorescence after the induction, were transiently transformed. Control and untransfected protoplasts showed red autofluorescence from chlorophyll. GFP expression was visible with 1 μM ABA (data not shown).

In addition, after electroporation of the plasmid DNA carrying HVA1-SGFP into maize leaf protoplasts, the expression of GFP was found to be enhanced by cold, high salt, dark, and ABA (FIG. 1). These responses were specific to HVA1-SGFP because the expression of an internal control, generated by fusing the maize ubiquitin promoter (Christensen et al., Plant Mol. Biol. 18:675, 1992) and the β-glucuronidase gene (UBI-GUS) (Jefferson, Plant Mol. Biol. Rep. 5:387, 1987), was not affected (data not shown). In addition, the GFP expression derived from UBI-SGFP was not changed by the same treatments (data not shown).

Intracellular $Ca^{2+}$ Elevation Activates Stress Signaling

The role of $Ca^{2+}$ as a second messenger in multiple stress responses was also studied. The effects of increased intracellular $Ca^{2+}$ on HVA1-SGFP expression in maize leaf protoplasts using $Ca^{2+}$ ionophore was examined using standard methods as described below (Knight et al., Nature 352:524, 1991; Schroeder and Thuleau, Plant Cell 3:555, 1991; Braam, Proc. Natl. Acad. Sci. U.S.A. 89:3213, 1992; McAinsh et al., Plant Cell 4:1113, 1992; Assmann, Ann. Rev. Cell Biol. 9:345, 1993; Poovaiah and Reddy, Crit. Rev. Plant Sci. 12:185, 1993; Trewavas and Knight, Plant Mol. Biol. 26:1329, 1994; Ward and Schroeder, Plant Cell 6:669, 1994; Bethke et al., in *Plant Hormones*, Davies, Ed., (Kluwer Academic 1995) pp. 298–317; Bush, Ann. Rev. Plant Physiol. Plant Mol. Biol. 46:95, 1995; Monroy and Dhindsa, Plant Cell 7:32, 1995; and Knight et al., Plant Cell 8:489, 1996).

Figure 2:
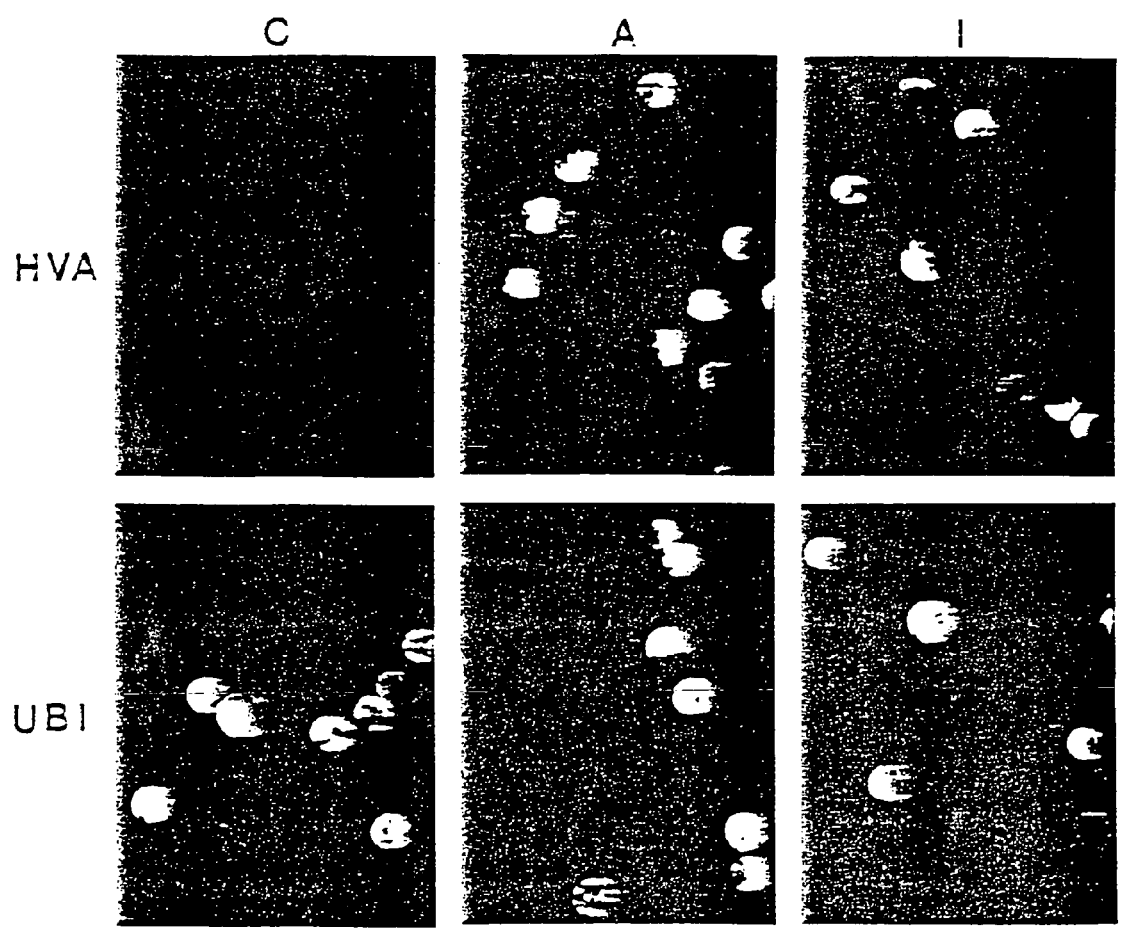
FIG. 2 shows a series of photographs demonstrating that intracellular $Ca^{2+}$ elevation activates stress signaling.

Maize leaf protoplasts transfected with HVA1-SGFP (HVA) or UBI-SGFP (UBI) were treated with 1 mM $Ca^{2+}$, 1 mM $Ca^{2+}$/100 nM A23187, and 1 mM $Ca^{2+}$/100 nM ionomycin, respectively designated "C," "A," and "I" in FIG. 2. UBI-SGFP was constructed by inserting the UBI promoter from pAHC27 (Christensen et al., Plant Mol. Biol. 18:675, 1992) into the SGFP vector (Chiu et al., Curr. Biol. 6:225, 1996). Protoplast transient expression is the same as described by Sheen (EMBO J. 12:3497, 1993) and Chiu et al. (Curr. Biol. 6:225,1996). About $10^5$ protoplasts from each treatment were observed using a fluorescence microscope (Chiu et al., Curr. Biol. 6:225, 1996). The experiment was repeated twice with similar results.

As shown in FIG. 2, the expression of HVA1-GFP was significantly increased by the $Ca^{2+}$/ionomycin and $Ca^{2+}$/A23187, but not by $Ca^{2+}$ alone in the incubation medium. This activation is specific because the same treatment did not influence UBI-SGFP expression (FIG. 2), but was found to inhibit the expression of GFP controlled by a stress-repressible photosynthetic gene promoter (Sheen, EMBO J. 12:3497, 1993; data not shown).

Constitutive ATCDPK1 and ATCDPK1a Activate Stress Signal Transduction

To determine whether $Ca^{2+}$ activated protein kinases (PKs) play a role in stress signal transduction in plants, the effect of co-expressing four constitutively active $Ca^{2+}$-dependent protein kinases (CDPKs) on the HVA1 promoter activity was examined. As is shown in FIG. 3A, plant CDPKs share extensive sequence identity with the mammalian multifunctional $Ca^{2+}$/calmodulin-dependent KPII (CaMKII) (Kapiloff et al., Proc. Natl. Acad. Sci. USA 88:3710, 1991). However, instead of bearing a calmodulin binding site, this family of PKs carries a calmodulin-like domain at the C-terminus (FIG. 3A). This unique feature presumably allows CDPKs to respond to $Ca^{2+}$ signals directly without calmodulin. Various other domains found in CaMKII and CDPK are shown in FIG. 3A, these include: (H) hinge, (N) $NH_2$_ terminal domain for some CDPKs (J) junction, (EF) EF-hand $Ca^{2+}$-binding site (Harper et al., Science 252:951, 1991; Suen and Choi, Plant Mol. Biol. 17:581, 1991; Roberts and Harmon, Ann. Rev. Plant Physiol. Plant Mol. Biol. 43:375, 1992; Estruch et al., Proc. Natl. Acad. Sci. USA 91:8837, 1994; Urao et al., Plant Physiol. 105:1461, 1994; Urao et al., Mol. Gen. Genet. 244:331, 1994; Harper et al., Bioch. 33:7267, 1994; and Kapiloff et al., Proc. Natl. Acad. Sci. USA 88:3710, 1991). Currently, CDPKs are the most prevalent serine/threonine PKs found in higher plants as the cloning of numerous CDPKs in a broad range of plant species has been reported (Harper et al., Science 252:951, 1991; Suen and Choi, Plant Mol. Biol. 17:581, 1991; Roberts and Harmon, Ann. Rev. Plant Physiol. Plant Mol. Biol. 43:375, 1992; Estruch et al., Proc. Natl. Acad. Sci. USA 91:8837, 1994; Urao et al., Plant Physiol. 105:1461, 1994; Urao et al., Mol. Gen. Genet. 244:331, 1994; Harper et al., Biochem. 33:7267, 1994).

Eight *Arabidopsis* PKs with full-length coding sequences were chosen for the following experiments (Urao et al., Mol. Gen. Genet. 244:331, 1994; Harper et al., Bioch. 33:7267, 1994; Minet et al., Plant J. 2:417, 1992; Anderberg and Walker-Simmons, Proc. Natl. Acad. Sci. USA 89:10183, 1992; Park et al., Plant Mol. Biol. 22:615, 1993; Holappa and Walker-Simmons, Plant Physiol. 108:1203, 1995).

Two CDPKs (ATCDPK1 and ATCDPK1a) are closely related (96% amino acid and similarity) while the other two CDPKs (AK1/ATCDPK and ATCDPK2) have more divergent sequences (78% and 75% amino acid similarity respectively, to ATCDPK1) (FIG. 3B). In vitro assays showed that AK1/ATCDPK and ATCDPK2 possess calcium-dependent PK activity and the truncated AK1/ATCDPK has calcium-independent (constitutively active) PK activity by (Urao et al., Mol. Gen. Genet. 244:331, 1994; and Harper et al., Bioch. 33:7267, 1994). The PK activity of ATCDPK1, however, has not been demonstrated in vitro because it does not phosphorylate common PK substrates (Urao et al., Mol. Gen. Genet. 244:331, 1994). The ATCDPK1a cDNA that has restriction enzyme digestion patterns distinct from those of ATCDPK1, was identified during the isolation of ATCDPK1 by polymerase chain reaction (PCR) (Minet et al., Plant J. 2:417,1992). The nucleotide and amino acid sequences of the ATCDPK1a PK are shown in FIG. 5 (SEQ ID NO: 1 and 2, respectively). The effect of four other *Arabidopsis* PKs (ATTPKa, ATPKb, ASKQ, ASK2) that share significant homology with the ABA-inducible PK (PKABA1), speculated to mediate ABA signal transduction, were also tested (Anderberg and Walker-Simmons, Proc. Natl. Acad. Sci. USA 89:10183, 1992; Park et al., Plant Mol. Biol. 22:615, 1993; Holappa and Walker-Simmons, Plant Physiol. 108: 1203, 1995). These PK cDNAs were obtained by PCR, and at least two clones of each cDNA were used for transient expression analysis. PK cDNAs were obtained by PCR using an *Arabidopsis* cDNA library. The primers for these reactions were: (AK1/ATCDPK) 5'-GAAGATCTATGGG-TAATACTTGTGTTGGA-3' (SEQ ID NO: 3) and 5'-GT-CAAGGCCTGTCGACTTGAACCCATGG-3' (SEQ ID NO: 4); (ATCDPK1) and (ATCDPKA1a) 5'-GCGGATC-CATGGCTAATCAAACTCAGATCAGCG-3' (SEQ ID NO: 5) and 5'-GTCAAGGCCTCATCAGTGAGAACAT-GTTC-3' (SEQ ID NO: 6); (ATCDPK2) 5'-GCGGATC-CATGGAGACGAAGCCAAACCCTA-3' (SEQ ID NO: 7) and 5'-GTCAAGGCCTTGCTTGTTCATCGACAATCC-3' (SEQ ID NO: 8); (ATPKa) 5'-CATGCCATGGCTCCGGC-GACTAATTCACCG-3' (SEQ ID NO: 9) and 5'-GTCAAG-GCCTATTCTTCAAGAACCATTTATCG-3' (SEQ ID NO: 10); (ATPKb) 5'GCGGATCCATGGCTCGAGCTCCGGT-GACCA-3 (SEQ ID NO: 11) and 5'-GTCAAGGCCTAT-TCTTCAAGAACCAACTATG-3' (SEQ ID NO: 12); (ASK1) 5'-GCGGATCCATGGCTAAGTCAGAGCTGGT-GAAAG-3' (SEQ ID NO: 13) and 5'-GTCAAGGCCTAT-TCTTTAGGAACCATGAATG-3' (SEQ ID NO: 14); (ASK2 5'-GCGGATCCATGGCTAAGTATGACGTTGT-CAAGG-3' (SEQ ID NO: 15) and GTCAAGGCCTATTCT-TCAAGTACCACGG-3' (SEQ ID NO: 16). The sequence of ATCDPKA1a was determined for both strands using an automatic sequencing facility.

Truncated forms containing all eleven PK domains, analogous to the construction of a constitutively active mutant of CaMKII in mammals (Kapiloff et al., Proc. Natl. Acad. Sci. 88, 7267, 1994) (FIG. 3A and FIG. 3B), were inserted into the plant expression vector with a strong constitutive promoter 35SC4PPDK (Sheen, EMBO J 12:3497, 1993; Chiu et al. Curr. Biol. 6:225,1996). The putative regulatory domains of theses PKs were deleted (FIG. 3C). To allow convenient monitoring of protein expression, these PKs were fused in frame to a double hemagglutinin (HA) epitope tag (designated DHA in FIG. 3C) at the C-terminus and inserted into a plant expression vector (Sheen, EMBO J. 12:3497, 1993; and Chiu et al., Curr. Biol. 6:225, 1996).

The expression of eight PKs in transfected maize leaf protoplasts were demonstrated by immunoprecipitation of [$^{35}$S] methionine labeled proteins with the anti-HA monoclonal antibody (FIG. 3D). Transfected protoplasts were incubated for four hours to allow mRNA accumulation and then labeled with 200 μCi/ml of [$^{35}$S] methionine for twelve hours before harvest. Immunoprecipitation was carried out based on a published protocol by Kapiloff et al. (Proc. Natl. Acad. Sci. USA 88:3710, 1991). The proteins were separated on a 12.5% SDS-PAGE gel and visualized by fluorography. All PK constructs yielded strong bands, approximately 30–35 kD for 2–8 and around 55 kD for AK1/ATCDPK, indicating that all transgenes were expressed efficiently (FIG. 3D).

For quantitating the effect of various constitutive PKs on stress signaling, another chimeric gene with the HVA1 promoter and the luciferase coding sequence (Leuhrsen et al., Meth. Enz. 216:397, 1992) (HVA1-LUC) was generated. Co-expression experiments were performed by electroporating the reporter (HVA1-LUC) and the effector (35SC4PSK-PK-HA) plasmids together into maize leaf protoplasts as follows.

Maize leaf protoplasts were transfected with HVA1-LUC alone and incubated without (FIG. 3E, "C") or with 100 μM ABA (FIG. 3E, "A"). HVA1-LUC was also co-electroporated with the PK constructs (1–8) shown in FIG. 3C and FIG. 3D, and incubated without ABA (FIG. 3E, "1–8"). Relative LUC activities from duplicated samples are shown. About 2% of the cell lysates were used for LUC (Luehrsen et al., Meth. Enz. 216:397, 1992) and GUS assays (Sheen, EMBO J. 12:3497, 1993; and Jefferson, Plant Mol. Biol. Rep. 5:387, 1987). The experiment was repeated three times with similar results.

The results showed that ATCDPK1 and ATCDPK1a, but not the other six PKs, could specifically activate LUC expression controlled by the HVA1 promoter (FIG. 3E). An identical set of PKs without the HA tag gave the same results (data not shown). The expression of UBI-GUS as an internal control was not affected (data not shown).

CDPK1 Activates but PP2C Abolishes Stress Signaling

To show that PK activity is important for the activation of the stress-inducible HVA1 promoter, a null mutation was made by site-directed mutagenesis to eliminate the ATP binding site (K40) in ATCDPK1 (Urao et al., Mol. Gen. Genet. 244:331, 1994; and Kapiloff et al., Proc. Natl. Acad. Sci. USA 88:3710, 1991) and analyzed as follows. Maize leaf protoplasts were electroporated with HVA1-SGFP alone, or with ATCDPK1 (CDPK1) and the ATCDPK1 (K40M) mutant (CDPK1mut). About $10^5$ protoplasts from each treatment were observed using a fluorescence microscope (Chiu et al., Curr. Biol. 6:225, 1996). About 50% of the protoplasts were transiently transformed.

The kinase mutation (K40M) did not affect the expression of the protein (FIG. 4A), but it could no longer activate the expression of HVA1-GFP (FIG. 4B). The expression of UBI-SGFP was not affected by ATCDPK1 or the ATCDPK1 mutant (data not shown). This result indicates that the PK domain of ATCDPK1 was required and sufficient to recognize specific protein substances mediating stress signal transduction. The deleted regulatory domain was likely involved in PK activity control in response to stress signals (Harper et al., Science 252:951, 1991; Suen and Choi, Plant Mol. Biol. 17:581, 1991; Roberts and Harmon, Ann. Rev. Plant Physiol. Plant Mol. Biol. 43:375, 1992; Estruch et al., Proc. Natl. Acad. Sci. USA 91:8837, 1994; Urao et al., Plant Physiol. 105:1461, 1994; Urao et al., Mol. Gen. Genet. 244:331, 1994; Harper et al., Bioch. 33:7267, 1994; and Kapiloff et al., Proc. Natl. Acad. Sci. USA 88:3710, 1991).

To further support the idea that ATCDPK1 and ATCDPK1a are positive regulators in plant stress signal transduction, the effect of a specific and constitutively active *Arabidopsis* protein phosphatase 2C (PP2C) capable of abolishing ABA responses (Leung et al., Science 264:1448, 1994; Meyer et al., Science 264:1452, 1994; Armstrong et al., Proc. Natl. Acad. Sci. USA 92:9520, 1995) was examined as follows. Maize leaf protoplasts were electroporated with HVA1-LUC alone or with the effectors as indicated. PP2C null did not show PP2C activity (data not shown). The experiments with the constitutively active PP2C or the null PP2C were performed with two concentrations of plasmid DNA (+, 20 μg and ++, 60 μg) (FIG. 4C). LUC and GUS assays were performed with 2% of the cell lysates as described previously by Sheen (EMBO J. 12:3497, 1993; Jefferson, Plant Mol. Biol. Rep. 5:387, 1987; and Luehrsen et al., Meth. Enz. 216:397, 1992). Relative LUC activities from duplicated samples are shown. The experiment was repeated three times with similar results (FIG. 4C).

HVA1-LUC expression activated by ABA was significantly repressed by the constitutively active PP2C. Constitutive PP2C, but not its null version diminished, but did not completely abolish, HVA1-LUC expression enhanced by ATCDPK1 (FIG. 4C). Other serine/threonine PPs such as PP1, PP2A and PP2B might be required to completely counteract the effect of ATCDPK1, which could be a convergent point of multiple stress signaling (FIG. 4D). The same results were obtained with ATCDPK1A, and the expression of the internal control UBI-GUS were not affected (data not shown). As the genes involved in stress responses are highly conserved in plants, the role of ATCDPK1 and ATCDPK1a in stress signal transduction may extend to various cell types of diverse plant species (FIG. 4D). Thus, the manipulation of specific CDPK activities might have important agricultural applications in preventing and protecting crop plants from stress damage and yield loss.

Isolation of Regulators of the Stress Signal Transduction Response

The isolation of additional stress regulator coding sequences (e.g., CDPK, PK, and CaM-K) having the ability to regulate the stress signal transduction pathway in plants is accomplished using standard strategies and techniques that are well known in the art.

In one particular example, the CDPK sequences described herein may be used, together with conventional screening methods of nucleic acid hybridization screening. Such hybridization techniques and screening procedures are well known to those skilled in the art and are described, for example, in Benton and Davis, Science 196:180, 1977; Grunstein and Hogness, Proc. Natl. Acad. Sci., USA 72:3961, 1975; Ausubel et al. *Current Protocols in Molecular Biology*, Wiley Interscience, New York, and Berger and Kimmel, *Guide to Molecular Cloning Techniques*, 1987, Academic Press, New York.;; and Sambrook et al., *Molecular Cloning: A Laboratory Manual*, Cold Spring Harbor Laboratory Press, New York. In one particular example, all or part of the CDPK (described herein) may be used as a probe to screen a recombinant plant DNA library for genes having sequence identity to the CDPK gene or the PK domain. Hybridizing sequences are detected by plaque or colony hybridization according to the methods described below.

Alternatively, using all or a portion of the amino acid sequence of the PK polypeptide (SEQ ID NO: 2), one may readily design PK-specific oligonucleotide probes, including PK degenerate oligonucleotide probes (i.e., a mixture of all possible coding sequences for a given amino acid sequence). These oligonucleotides may be based upon the sequence of either DNA strand and any appropriate portion of the PK sequence. General methods for designing and preparing such probes are provided, for example, in Ausubel et al., 1996, *Current Protocols in Molecular Biology*, Wiley Interscience, New York, and Berger and Kimmel, *Guide to Molecular Cloning Techniques*, 1987, Academic Press, New York. These oligonucleotides are useful for PK gene isolation, either through their use as probes capable of hybridizing to PK complementary sequences or as primers for various amplification techniques, for example, polymerase chain reaction (PCR) cloning strategies. If desired, a combination of different oligonucleotide probes may be used for the screening of a recombinant DNA library. The oligonucleotides may be detectably-labeled using methods known in the art and used to probe filter replicas from a recombinant DNA library. Recombinant DNA libraries are prepared according to methods well known in the art, for example, as described in Ausubel et al. (supra), or they may be obtained from commercial sources.

As discussed above, PK oligonucleotides may also be used as primers in amplification cloning strategies, for example, using PCR. PCR methods are well known in the art and are described, for example, in *PCR Technology*, Erlich, ed., Stockton Press, London, 1989; *PCR Protocols: A Guide to Methods and Applications*, Innis et al., eds., Academic Press, Inc., New York, 1990; and Ausubel et al. (supra). Primers are optionally designed to allow cloning of the amplified product into a suitable vector, for example, by including appropriate restriction sites at the 5' and 3' ends of the amplified fragment (as described herein). If desired, PK sequences may be isolated using the PCR "RACE" technique, or Rapid Amplification of cDNA Ends (see, e.g., Innis et al. (supra)). By this method, oligonucleotide primers based on an PK sequence are oriented in the 3' and 5' directions and are used to generate overlapping PCR fragments. These overlapping 3'- and 5'-end RACE products are combined to produce an intact full-length cDNA. This method is described in Innis et al. (supra); and Frohman et al., Proc. Natl. Acad. Sci. USA 85:8998, 1988.

Confirmation of a sequence's relatedness to the PK polypeptide family may be accomplished by a variety of conventional methods including, but not limited to, sequence comparison of the gene and its expressed product. In addition, the activity of the gene product may be evaluated according to any of the techniques described.

Once a regulator of the stress response is identified (e.g., CDPK, PK, or CaM-K sequences), it is cloned according to standard methods and used for the construction of plant expression vectors as described below.

Expression Constructs Encoding Regulators of the Stress Signal Transduction Response Those skilled in the field of molecular biology will understand that any of a wide variety of expression systems may be used to provide the recombinant protein. The precise host cell used is not critical to the invention. The regulators of the invention (e.g., a CDPK, a PK domain, or a CaM-K) may be produced in a prokaryotic host, for example, *E. coli*, or in a eukaryotic host, for example, *Saccharomyces cerevisiae*, mammalian cells (for example, COS 1 or NIH 3T3 cells), or any of a number of plant hosts including, without limitation, algae, tree species, ornamental species, temperate fruit species, tropical fruit species, vegetable species, legume species, crucifer species, monocots, dicots, or in any plant of commercial or agricultural significance. Particular examples of suitable plant hosts include, but are not limited to, Conifers, Petunia, Tomato, Potato, Tobacco, *Arabidopsis*, Lettuce, Sunflower, Oilseed rape, Flax, Cotton, Sugarbeet, Celery, Soybean, Alfalfa, *Medicago*, Lotus, *Vigna*, Cucumber, Carrot, Eggplant, Cauliflower, Horseradish, Morning Glory, Poplar, Walnut, Apple, Grape, Asparagus, Rice, Maize, Millet, Onion, Barley, Orchard grass, Oat, Rye, and Wheat. In addition, as is discussed below, expression constructs may be expressed in a transgenic plant to turn on the stress signal transduction pathway to enhance plant tolerance to multiple stress conditions.

Materials for expressing these genes are available from a wide range of sources including the American Type Culture Collection (Rockland, Md.); or from any of a number seed companies, for example, W. Atlee Burpee Seed Co. (Warminster, Pa.), Park Seed Co. (Greenwood, S.C.), Johnny Seed Co. (Albion, Me.), or Northrup King Seeds (Harstville, S.C.). Descriptions and sources of useful host cells are also found in Vasil I. K., Cell Culture and Somatic Cell Genetics of Plants, Vol I, II, III Laboratory Procedures and Their Applications Academic Press, New York, 1984; Dixon, R. A., Plant Cell Culture-A Practical Approach, IRL Press, Oxford University, 1985; Green et al., Plant Tissue and Cell Culture, Academic Press, New York, 1987; and Gasser and Fraley, Science 244:1293, 1989.

The method of transformation or transfection and the choice of vehicle for expression of the regulator polypeptide (e.g., a CDPK, a PK domain, or a CaM-K) will depend on the host system selected. Transformation and transfection methods are described, e.g., in Ausubel et al. (supra); Weissbach and Weissbach, Methods for Plant Molecular Biology, Academic Press, 1989; Gelvin et al., Plant Molecular Biology Manual, Kluwer Academic Publishers, 1990; Kindle, K., Proc. Natl. Acad. Sci., U.S.A 87:1228, 1990; Potrykus, I., Annu. Rev. Plant Physiol. Plant Mol. Biology 42:205, 1991; and BioRad (Hercules, Calif.) Technical Bulletin #1687 (Biolistic Particle Delivery Systems). Expression vehicles may be chosen from those provided, e.g., in Cloning Vectors: A Laboratory Manual (P. H. Pouwels et al., 1985, Supp. 1987); Gasser and Fraley (supra); Clontech Molecular Biology Catalog (Catalog 1992/93 Tools for the Molecular Biologist, Palo Alto, Calif.); and the references cited above. Other expression constructs are described by Fraley et al. (U.S. Pat. No. 5,352,605).

Most preferably, a regulator polypeptide (e.g. CDPK, PK domain, or CaM-K) is produced by a stably-transfected plant cell line, a transiently-transfected plant cell line, or by a transgenic plant. A number of vectors suitable for stable transfection of plant cells or for the establishment of transgenic plants are available to the public; such vectors are described in Pouwels et al. (supra), Weissbach and Weissbach (supra), and Gelvin et al. (supra). Methods for constructing such cell lines are described in, e.g., Weissbach and Weissbach (supra), and Gelvin et al. (supra). Typically, plant expression vectors include (1) a cloned plant gene under the transcriptional control of 5' and 3' regulatory sequences and (2) a dominant selectable marker. Such plant expression vectors may also contain, if desired, a promoter regulatory region (for example, one conferring inducible or constitutive, pathogen- or wound-induced, environmentally- or developmentally-regulated, or cell- or tissue-specific expression), a transcription initiation start site, a ribosome binding site, an RNA processing signal, a transcription termination site, and/or a polyadenylation signal.

Once the desired nucleic acid sequence encoding a regulator polypeptide (e.g., CDPK, PK, or CaM-K sequence) is obtained as described above, it may be manipulated in a variety of ways known in the art. For example, where the sequence involves non-coding flanking regions, the flanking regions may be subjected to mutagenesis.

The regulator DNA sequence of the invention may, if desired, be combined with other DNA sequences in a variety of ways. The regulator DNA sequence of the invention may be employed with all or part of the gene sequences normally associated with itself. In its component parts, a DNA sequence encoding a regulator polypeptide (e.g., a CDPK, a PK domain, or a CaM-K) is combined in a DNA construct having a transcription initiation control region capable of promoting transcription and translation in a host cell.

In general, the constructs will involve regulatory regions functional in plants which provide for modified production of the regulator protein as discussed herein. The open reading frame coding for the regulator protein or functional fragment thereof will be joined at its 5' end to a transcription initiation regulatory region such as the sequence naturally found in the 5' upstream region of the regulator structural gene (e.g., CDPK, PK domain, or CaM-K). Numerous other transcription initiation regions are available which provide for constitutive or inducible regulation.

For applications where developmental, cell, tissue, hormonal, or environmental expression is desired, appropriate 5' upstream non-coding regions are obtained from other genes, for example, from genes regulated during meristem development, seed development, embryo development, or leaf development.

Regulatory transcript termination regions may also be provided in DNA constructs of this invention as well. Transcript termination regions may be provided by the DNA sequence encoding the regulator protein (e.g., CDPK, PK domain, or CaM-K) or any convenient transcription termination region derived from a different gene source. The transcript termination region will contain preferably at least 1–3 kb of sequence 3' to the structural gene from which the termination region is derived. Plant expression constructs having, for example, CDPK as the DNA sequence of interest for expression may be employed with a wide variety of plant life. Such genetically-engineered plants are useful for a variety of industrial and agricultural applications as discussed herein. Importantly, this invention is applicable to dicotyledons and monocotyledons, and will be readily applicable to any new or improved transformation or regeneration method.

An example of a useful plant promoter according to the invention is a caulimovirus promoter, for example, a cauliflower mosaic virus (CaMV) promoter. These promoters confer high levels of expression in most plant tissues, and the activity of these promoters is not dependent on virally encoded proteins. CaMV is a source for both the 35S and 19S promoters. In most tissues of transgenic plants, the CaMV 35S promoter is a strong promoter (see, e.g., Odell et al., Nature 313:810, 1985). The CaMV promoter is also highly active in monocots (see, e.g., Dekeyser et al., Plant Cell 2:591, 1990; Terada and Shimamoto, *Mol. Gen. Genet.* 220:389, 1990). Moreover, activity of this promoter can be further increased (i.e., between 2–10 fold) by duplication of the CaMV 35S promoter (see e.g., Kay et al., Science 236:1299, 1987; Ow et al., *Proc. Natl. Acad. Sci., U.S.A.* 84:4870, 1987; and Fang et al., Plant Cell 1:141, 1989).

Other useful plant promoters include, without limitation, the nopaline synthase promoter (An et al., Plant Physiol. 88:547, 1988) and the octopine synthase promoter (Fromm et al., Plant Cell 1:977, 1989).

For certain applications, it may be desirable to produce the regulator gene product (e.g., CDPK, PK domain, or CaM-K) in an appropriate tissue, at an appropriate level, or at an appropriate developmental time. For this purpose, there are an assortment of gene promoters, each with its own distinct characteristics embodied in its regulatory sequences, shown to be regulated in response to the environment, hormones, and/or developmental cues. These include gene promoters that are responsible for heat-regulated gene expression (see, e.g., Callis et al., Plant Physiol. 88:965, 1988; Takahashi and Komeda, Mol. Gen. Genet. 219:365, 1989; and Takahashi et al., Plant J. 2:751, 1992), light-regulated gene expression (e.g., the pea rbcS-3A described by Kuhlemeier et al., Plant Cell 1:471, 1989; the maize rbcS promoter described by Schäffner and Sheen, Plant Cell 3:997, 1991; or the cholorphyll a/b-binding protein gene found in pea described by Simpson et al., EMBO J. 4:2723, 1985), hormone-regulated gene expression (for example, the abscisic acid (ABA) responsive sequences from the Em gene of wheat described by Marcotte et al., Plant Cell 1:969, 1989; the ABA-inducible HVA1 and HVA22, and rd29A promoters described for barley and *Arabidopsis* by Straub et al., Plant Cell 6:617, 1994, Shen et al., Plant Cell 7:295, 1995; and wound-induced gene expression (for example, of wunI described by Siebertz et al., Plant Cell 1:961, 1989), organ-specific gene expression (for example, of the tuber-specific storage protein gene described by Roshal et al., EMBO J. 6:1155, 1987; the 23-kDa zein gene from maize described by Schernthaner et al., EMBO J. 7:1249, 1988; or the French bean β-phaseolin gene described by Bustos et al., Plant Cell 1:839, 1989), or pathogen-inducible promoters (for example, PR-1 or β-1,3 glucanase promoters).

Plant expression vectors may also optionally include RNA processing signals, e.g, introns, which have been shown to be important for efficient RNA synthesis and accumulation (Callis et al., Genes and Dev. 1:1183, 1987). The location of the RNA splice sequences can dramatically influence the level of transgene expression in plants. In view of this fact, an intron may be positioned upstream or downstream of a CDPK, Cam-K, or PK domain polypeptide-encoding sequence in the transgene to modulate levels of gene expression.

In addition to the aforementioned 5' regulatory control sequences, the expression vectors may also include regulatory control regions which are generally present in the 3' regions of plant genes (Thornburg et al., Proc. Natl. Acad. Sci. U.S.A. 84:744, 1987; An et al., Plant Cell 1:115, 1989). For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin, or spectinomycin. Genes required for photosynthesis may also be used as selectable markers in photosynthetic-deficient strains. Finally, genes encoding herbicide resistance may be used as selectable markers; useful herbicide resistance genes include the bar gene encoding the enzyme phosphinothricin acetyltransferase and conferring resistance to the broad spectrum herbicide Basta® (Hoechst AG, Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 75–100 µg/mL (kanamycin), 20–50 µg/mL (hygromycin), or 5–10 µg/mL (bleomycin). A useful strategy for selection of transformants for herbicide resistance is described, e.g., by Vasil et al., supra.

It should be readily apparent to one skilled in the art of molecular biology, especially in the field of plant molecular biology, that the level of gene expression is dependent, not only on the combination of promoters, RNA processing signals, and terminator elements, but also on how these elements are used to increase the levels of selectable marker gene expression.

Plant Transformation

Upon construction of the plant expression vector, several standard methods are available for introduction of the vector into a plant host, thereby generating a transgenic plant. These methods include (1) Agrobacterium-mediated transformation (*A. tumefaciens* or *A. rhizogenes*) (see, e.g., Lichtenstein and Fuller, In: Genetic Engineering, vol 6, P W J Rigby, ed, London, Academic Press, 1987; and Lichtenstein, C. P., and Draper, J,. In: *DNA Cloning*, Vol II, D. M. Glover, ed, Oxford, IRI Press, 1985)), (2) the particle delivery system (see, e.g., Gordon-Kamm et al., Plant Cell 2:603 (1990); or BioRad Technical Bulletin 1687, supra), (3) microinjection protocols (see, e.g., Green et al., supra), (4) polyethylene glycol (PEG) procedures (see, e.g., Draper et al., Plant Cell Physiol. 23:451, 1982; or e.g., Zhang and Wu, Theor. Appl. Genet. 76:835, 1988), (5) liposome-mediated DNA uptake (see, e.g., Freeman et al., Plant Cell Physiol. 25:1353, 1984), (6) electroporation protocols (see, e.g., Gelvin et al., supra; Dekeyser et al., supra; Fromm et al., Nature 319:791, 1986; Sheen, Plant Cell 2:1027, 1990; or Jang and Sheen, Plant Cell 6:1665, 1994), and (7) the vortexing method (see, e.g., Kindle supra). The method of transformation is not critical to the invention. Any method which provides for efficient transformation may be employed. As newer methods are available to transform crops or other host cells, they may be directly applied.

The following is an example outlining one particular technique, an *Agrobacterium*-mediated plant transformation. By this technique, the general process for manipulating genes to be transferred into the genome of plant cells is carried out in two phases. First, cloning and DNA modification steps are carried out in *E. coli*, and the plasmid containing the gene construct of interest is transferred by conjugation or electroporation into *Agrobacterium*. Second, the resulting *Agrobacterium* strain is used to transform plant cells. Thus, for the generalized plant expression vector, the plasmid contains an origin of replication that allows it to replicate in *Agrobacterium* and a high copy number origin of replication functional in *E. coli*. This permits facile production and testing of transgenes in *E. coli* prior to transfer to *Agrobacterium* for subsequent introduction into plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of *Agrobacterium*, delimit the DNA region that will be transferred to the plant.

In another example, plant cells may be transformed by shooting into the cell tungsten microprojectiles on which cloned DNA is precipitated. In the Biolistic Apparatus (Bio-Rad) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to pass through. As a result, the plastic macroprojectile smashes against the stopping plate, and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

In general, transfer and expression of transgenes in plant cells are now routine practices to those skilled in the art, and have become major tools to carry out gene expression studies in plants and to produce improved plant varieties of agricultural or commercial interest.

Transgenic Plant Regeneration

Plant cells transformed with a plant expression vector can be regenerated, for example, from single cells, callus tissue, or leaf discs according to standard plant tissue culture techniques. It is well known in the art that various cells, tissues, and organs from almost any plant can be successfully cultured to regenerate an entire plant; such techniques are described, e.g., in Vasil supra; Green et al., supra; Weissbach and Weissbach, supra; and Gelvin et al., supra.

In one particular example, a cloned CDPK polypeptide (or PK domain or CaM-K) construct under the control of the nos promoter and the nopaline synthase terminator and carrying a selectable marker (for example, kanamycin resistance) is transformed into *Agrobacterium*. Transformation of leaf discs (for example, of tobacco or potato leaf discs), with vector-containing *Agrobacterium* is carried out as described by Horsch et al. (Science 227:1229, 1985). Putative transformants are selected after a few weeks (for example, 3 to 5 weeks) on plant tissue culture media containing kanamycin (e.g. 100 μg/mL). Kanamycin-resistant shoots are then placed on plant tissue culture media without hormones for root initiation. Kanamycin-resistant plants are then selected for greenhouse growth. If desired, seeds from self-fertilized transgenic plants can then be sowed in a soil-less medium and grown in a greenhouse. Kanamycin-resistant progeny are selected by sowing surfaced sterilized seeds on hormone-free kanamycin-containing media. Analysis for the integration of the transgene is accomplished by standard techniques (see, for example, Ausubel et al. supra; Gelvin et al. supra).

Transgenic plants expressing the selectable marker are then screened for transmission of the transgene DNA by standard immunoblot and DNA detection techniques. Each positive transgenic plant and its transgenic progeny are unique in comparison to other transgenic plants established with the same transgene. Integration of the transgene DNA into the plant genomic DNA is in most cases random, and the site of integration can profoundly affect the levels and the tissue and developmental patterns of transgene expression. Consequently, a number of transgenic lines are usually screened for each transgene to identify and select plants with the most appropriate expression profiles.

Transgenic lines are evaluated for levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for protein expression by Western immunoblot analysis using specific antibodies (see, e.g., Ausubel et al., supra). In addition, in situ hybridization and immunocytochemistry according to standard protocols can be done using transgene-specific nucleotide probes and antibodies, respectively, to localize sites of expression within transgenic tissue.

In addition, if desired, once the recombinant regulator protein (e.g., CDPK, PK domain, or CaM-K) is expressed in any cell or in a transgenic plant (for example, as described above), it may be isolated, e.g., using affinity chromatography. In one example, an anti-regulator polypeptide antibody (e.g., produced as described in Ausubel et al., supra, or by any standard technique) may be attached to a column and used to isolate the polypeptide. Lysis and fractionation of regulator-producing cells prior to affinity chromatography may be performed by standard methods (see, e.g., Ausubel et al., supra). Once isolated, the recombinant protein can, if desired, be further purified, for example, by high performance liquid chromatography (see, e.g., Fisher, Laboratory Techniques In Biochemistry And Molecular Biology, eds., Work and Burdon, Elsevier, 1980).

Engineering Stress-Protected Transgenic Plants

As discussed above, plasmid constructs designed for the expression of regulator gene products (e.g., a CDPK, a PK domain, or a CaM-K) are useful for generating transgenic plants having an increased level of tolerance to environmental stress. To achieve such tolerance, it is important to express a regulator gene product at an effective level. Evaluation of the level of stress protection conferred to a plant by expression of regulator gene is determined according to conventional methods and assays.

In one working example, constitutive expression of the PK domain gene in tomato is used to enhance salt stress tolerance. Specifically, a plant expression vector is constructed that contains a PK cDNA sequence expressed under the control of the nos promoter, a low constitutive promoter. This expression vector is then used to transform tomato according to standard methods. To assess salt tolerance, transformed tomato plants and appropriate controls are evaluated according to methods described in Lilus et al. (BioTechnology 14:177, 1996) and Tarczynski et al. (Science 259:508, 1993). Transformed tomato plants that express a PK domain gene having an increased level of salt tolerance relative to control plants are taken as being useful in the invention.

Use

The invention described herein is useful for a variety of agricultural and commercial purposes including, but not limited to, improving tolerance to a variety of environmental stresses, including but not limited to, drought, salinity, cold, and heat, increasing crop yields, improving crop and ornamental quality, and reducing agricultural production costs. In particular, expression of a regulator gene (e.g., a CDPK, a PK domain, or a CaM-K gene) in a plant cell provides tolerance to such stress and can be used to protect plants from adverse conditions that reduce plant productivity and viability. The invention therefore affords a means for producing plants that can live in environments where growth would otherwise be impaired by adverse environmental factors.

All publications and patent applications mentioned in this specification are herein incorporated by reference to the same extent as if each independent publication or patent application was specifically and individually indicated to be incorporated by reference.

What is claimed is:

1. A method for protecting a plant against dehydration, said method comprising the steps of:
   (a) providing a transgenic plant cell that expresses substantially pure DNA encoding a calcium-dependent protein kinase (CDPK) polypeptide that includes a protein kinase (PK) domain having a sequence that is at least 90% identical to SEQ ID NO: 2; and
   (b) growing a transgenic plant from said plant cell, wherein said DNA is expressed in said transgenic plant, and wherein said transgenic plant has increased tolerance to dehydration compared to a corresponding untransformed plant.

2. The method of claim 1, wherein the expression of said polypeptide activates the expression of a stress-protective protein-encoding gene.

3. The method of claim 1, wherein said DNA is constitutively expressed in said transgenic plant.

4. A plant comprising substantially pure DNA encoding a polypeptide that includes a PK domain having an amino acid sequence that is at least 90% identical to SEQ ID NO: 2, wherein said polypeptide increases drought tolerance in a plant expressing said polypeptide.

5. A seed comprising substantially pure DNA encoding a polypeptide that includes a PK domain having an amino acid sequence that is at least 90% identical to SEQ ID NO:2, wherein said polypeptide increases drought tolerance in a plant expressing said polypeptide.

6. A cell comprising substantially pure DNA encoding a polypeptide that includes a PK domain having an amino acid sequence that is at least 90% identical to SEQ ID NO:2, wherein said polypeptide increases drought tolerance in a plant expressing said polypeptide.

7. Substantially pure DNA consisting of a sequence that encodes a PK domain having an amino acid sequence that is at least 90% identical to SEQ ID NO: 2.

8. The DNA of claim 7, wherein said DNA encodes a polypeptide that confers tolerance to dehydration.

9. The DNA of claim 7, wherein said DNA encodes a polypeptide that confers tolerance to salinity.

10. The DNA of claim 7, wherein said DNA encodes a polypeptide that confers tolerance to a temperature stress.

11. The DNA of claim 7, wherein said DNA comprises a nucleic acid sequence substantially identical to the nucleic acid sequence of SEQ ID NO: 1.

12. The DNA of claim 7, wherein said DNA is operably linked to an expression control region.

13. The DNA of claim 12, wherein said expression control region comprises a promoter.

14. The DNA of claim 13, wherein said promoter is a constitutive promoter.

15. The DNA of claim 14, wherein said promoter is an inducible promoter.

16. A cell which includes the DNA of claim 7.

17. The cell of claim 16, wherein said cell is a plant cell.

18. The method of claim 1, wherein said calcium-dependent protein kinase (CDPK) polypeptide is ATCDPK1 or ATCDPK1a.

19. The plant of claim 4, wherein said calcium-dependent protein kinase (CDPK) polypeptide is ATCDPK1 or ATCDPK1a.

* * * * *

SEQUENCE LISTING

<160> NUMBER OF SEQ ID NOS: 18

<210> SEQ ID NO 1
<211> LENGTH: 1020
<212> TYPE: DNA
<213> ORGANISM: Arabidopsis thaliana
<220> FEATURE:
<221> NAME/KEY: variation
<222> LOCATION: (1)...(1020)
<223> OTHER INFORMATION: N is any nucleotide.

<400> SEQUENCE: 1

| | |
|---|---|
| gttgtaaaac gacggncagt gaattgtaat acgactcnct atagggcgna attggagctc | 60 |
| caccgcggtg gcggccgctc tagaactagt ggatcc atg gct aat caa act cag | 114 |
| atc agc gac aag tac atc tta gga cga gaa ctc ggt cgc ggc gaa ttc | 162 |
| gga atc acg tat ctt tgt aca gat aga gag act cgt gaa gct tta gct | 210 |
| tgc aaa tca atc tcc aag aga aag ctc cga acc gcc gtc gat gtg gaa | 258 |
| gac gtc cgt cgt gaa gtc acg atc atg tca act tta ccg gaa cac cca | 306 |
| aac gtt gtg aaa ctt aaa gcg act tat gag gat aac gag acc gtg cat | 354 |
| ctt gtg atg gag ctt tgt gaa gga ggt gag ctt ttt ggt cgg att gtt | 402 |
| gca aga gga cat tat aca gag cgt gcg gcg gct acc gtc gcg aga acg | 450 |
| atc gcg gaa gtt gtg agg atg tgt cat gtc aat ggt gtt atg cat aga | 498 |
| gat ttg aag cct gag aat ttc ttg ttt gct aac aag aag gag aat tct | 546 |
| gca ctt aag gct att gat ttt ggt tta tct gtt ctc ttt aaa cct gga | 594 |
| gag agg ttt aca gag att gtt gga agt cct tat tat atg gct cca gaa | 642 |
| gtg ttg aag aga aat tat gga cca gag gtt gat gtg tgg agt gct gga | 690 |
| gtt atc ctc tac atc ttg ctt tgt ggt gtt cct ccg ttt tgg gca gag | 738 |
| act gaa caa ggt gtg gct ctt gcc atc ttg agg gga gtt ctt gat ttt | 786 |
| aag aga gat cct tgg tcg cag ata tca gag agc gca aag agc ctt gtg | 834 |
| aag cag atg ttg gaa cct gat tca act aag cgt ttg act gct cag caa | 882 |
| gtt ctt gat cac cct tgg ata cag aat gca aag aaa aggatcaagc | 928 |
| ttatcgatac cgtcgacctc gagggggggc ccggtaccag ctttngttcc ctttagtgag | 988 |
| ggttaatttc gagcttggcg taatcatgtc at | 1020 |

<210> SEQ ID NO 2
<211> LENGTH: 274
<212> TYPE: PRT
<213> ORGANISM: Arabidopsis thaliana

<400> SEQUENCE: 2

Met Ala Asn Gln Thr Gln Ile Ser Asp Lys Tyr Ile Leu Gly Arg Glu
 1               5                  10                  15

Leu Gly Arg Gly Glu Phe Gly Ile Thr Tyr Leu Cys Thr Asp Arg Glu
             20                  25                  30

Thr Arg Glu Ala Leu Ala Cys Lys Ser Ile Ser Lys Arg Lys Leu Arg
         35                  40                  45

Thr Ala Val Asp Val Glu Asp Val Arg Arg Glu Val Thr Ile Met Ser
     50                  55                  60

```
Thr Leu Pro Glu His Pro Asn Val Val Lys Leu Lys Ala Thr Tyr Glu
 65                  70                  75                  80

Asp Asn Glu Thr Val His Leu Val Met Glu Leu Cys Glu Gly Gly Glu
             85                  90                  95

Leu Phe Gly Arg Ile Val Ala Arg Gly His Tyr Thr Glu Arg Ala Ala
        100                 105                 110

Ala Thr Val Ala Arg Thr Ile Ala Glu Val Val Arg Met Cys His Val
    115                 120                 125

Asn Gly Val Met His Arg Asp Leu Lys Pro Glu Asn Phe Leu Phe Ala
130                 135                 140

Asn Lys Lys Glu Asn Ser Ala Leu Lys Ala Ile Asp Phe Gly Leu Ser
145                 150                 155                 160

Val Leu Phe Lys Pro Gly Glu Arg Phe Thr Glu Ile Val Gly Ser Pro
                165                 170                 175

Tyr Tyr Met Ala Pro Glu Val Leu Lys Arg Asn Tyr Gly Pro Glu Val
            180                 185                 190

Asp Val Trp Ser Ala Gly Val Ile Leu Tyr Ile Leu Leu Cys Gly Val
        195                 200                 205

Pro Pro Phe Trp Ala Glu Thr Glu Gln Gly Val Ala Leu Ala Ile Leu
    210                 215                 220

Arg Gly Val Leu Asp Phe Lys Arg Asp Pro Trp Ser Gln Ile Ser Glu
225                 230                 235                 240

Ser Ala Lys Ser Leu Val Lys Gln Met Leu Glu Pro Asp Ser Thr Lys
                245                 250                 255

Arg Leu Thr Ala Gln Gln Val Leu Asp His Pro Trp Ile Gln Asn Ala
            260                 265                 270

Lys Lys

<210> SEQ ID NO 3
<211> LENGTH: 29
<212> TYPE: DNA
<213> ORGANISM: Arabidopsis thaliana

<400> SEQUENCE: 3
gaagatctat gggtaatact tgtgttgga                                29

<210> SEQ ID NO 4
<211> LENGTH: 28
<212> TYPE: DNA
<213> ORGANISM: Arabidopsis thaliana

<400> SEQUENCE: 4
gtcaaggcct gtcgacttga acccatgg                                 28

<210> SEQ ID NO 5
<211> LENGTH: 33
<212> TYPE: DNA
<213> ORGANISM: Arabidopsis thaliana

<400> SEQUENCE: 5
gcggatccat ggctaatcaa actcagatca gcg                           33

<210> SEQ ID NO 6
<211> LENGTH: 29
<212> TYPE: DNA
<213> ORGANISM: Arabidopsis thaliana
```

```
<400> SEQUENCE: 6
gtcaaggcct catcagtgag aacatgttc                              29

<210> SEQ ID NO 7
<211> LENGTH: 30
<212> TYPE: DNA
<213> ORGANISM: Arabidopsis thaliana

<400> SEQUENCE: 7
gcggatccat ggagacgaag ccaaaccccta                            30

<210> SEQ ID NO 8
<211> LENGTH: 30
<212> TYPE: DNA
<213> ORGANISM: Arabidopsis thaliana

<400> SEQUENCE: 8
gtcaaggcct tgcttgttca tcgacaatcc                             30

<210> SEQ ID NO 9
<211> LENGTH: 30
<212> TYPE: DNA
<213> ORGANISM: Arabidopsis thaliana

<400> SEQUENCE: 9
catgccatgg ctccggcgac taattcaccg                             30

<210> SEQ ID NO 10
<211> LENGTH: 32
<212> TYPE: DNA
<213> ORGANISM: Arabidopsis thaliana

<400> SEQUENCE: 10
gtcaaggcct attcttcaag aaccatttat cg                          32

<210> SEQ ID NO 11
<211> LENGTH: 30
<212> TYPE: DNA
<213> ORGANISM: Arabidopsis thaliana

<400> SEQUENCE: 11
gcggatccat ggctcgagct ccggtgacca                             30

<210> SEQ ID NO 12
<211> LENGTH: 31
<212> TYPE: DNA
<213> ORGANISM: Arabidopsis thaliana

<400> SEQUENCE: 12
gtcaaggcct attcttcaag aaccaactat g                           31

<210> SEQ ID NO 13
<211> LENGTH: 33
<212> TYPE: DNA
<213> ORGANISM: Arabidopsis thaliana

<400> SEQUENCE: 13
gcggatccat ggctaagtca gagctggtga aag                         33

<210> SEQ ID NO 14
<211> LENGTH: 31
<212> TYPE: DNA
<213> ORGANISM: Arabidopsis thaliana
```

-continued

```
<400> SEQUENCE: 14
gtcaaggcct attctttagg aaccatgaat g                                    31

<210> SEQ ID NO 15
<211> LENGTH: 33
<212> TYPE: DNA
<213> ORGANISM: Arabidopsis thaliana

<400> SEQUENCE: 15
gcggatccat ggctaagtat gacgttgtca agg                                  33

<210> SEQ ID NO 16
<211> LENGTH: 28
<212> TYPE: DNA
<213> ORGANISM: Arabidopsis thaliana

<400> SEQUENCE: 16
gtcaaggcct attcttcaag taccacgg                                        28

<210> SEQ ID NO 17
<211> LENGTH: 20
<212> TYPE: DNA
<213> ORGANISM: Hordeum vulgare

<400> SEQUENCE: 17
tccaccgaga tgccgacgca                                                 20

<210> SEQ ID NO 18
<211> LENGTH: 26
<212> TYPE: DNA
<213> ORGANISM: Hordeum vulgare

<400> SEQUENCE: 18
gttggaggcc atggtcgtct cacgat                                          26
```